US012577364B2

(12) United States Patent
Quirk

(10) Patent No.: US 12,577,364 B2
(45) Date of Patent: Mar. 17, 2026

(54) OPTIMIZATION OF A HALOPHILIC PHB DEPOLYMERASE FOR INDUSTRIAL APPLICATIONS

(71) Applicant: Kimberly-Clark Worldwide, Inc., Neenah, WI (US)

(72) Inventor: Stephen Quirk, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 18/558,880

(22) PCT Filed: May 28, 2021

(86) PCT No.: PCT/US2021/034848
§ 371 (c)(1),
(2) Date: Nov. 3, 2023

(87) PCT Pub. No.: WO2022/250694
PCT Pub. Date: Dec. 1, 2022

(65) Prior Publication Data
US 2024/0228729 A1 Jul. 11, 2024

(51) Int. Cl.
*C12N 9/18* (2006.01)
*C08J 11/10* (2006.01)
*C12N 15/70* (2006.01)

(52) U.S. Cl.
CPC ............... *C08J 11/105* (2013.01); *C12N 9/18* (2013.01); *C12N 15/70* (2013.01); *C12Y 301/01075* (2013.01)

(58) Field of Classification Search
CPC ...................................................... C08J 11/105
See application file for complete search history.

(56) References Cited

U.S. PATENT DOCUMENTS

| | | | |
|---|---|---|---|
| 5,968,801 | A | 10/1999 | Saito et al. |
| 7,858,353 | B2 | 12/2010 | Thompson et al. |
| 8,728,776 | B2 | 5/2014 | Ferreira et al. |
| 9,783,833 | B2 | 10/2017 | Pearlman et al. |
| 2003/0143703 | A1 | 7/2003 | Lee et al. |
| 2012/0171743 | A1 | 7/2012 | Hoang et al. |
| 2017/0013861 | A1 | 1/2017 | Nonato et al. |
| 2017/0253713 | A1 | 9/2017 | Ibrahim et al. |

FOREIGN PATENT DOCUMENTS

| | | | |
|---|---|---|---|
| CN | 1331607 | A | 1/2002 |
| CN | 105985939 | A | 10/2016 |
| CN | 106399200 | A | 2/2017 |
| CN | 110904161 | A | 3/2020 |
| EP | 3106513 | A1 | 12/2016 |
| JP | 2009207424 | A | 9/2009 |
| JP | 2013209587 | A | 10/2013 |
| KR | 20010089675 | A | 10/2001 |
| KR | 100429001 | B1 | 4/2004 |
| KR | 101118695 | B1 | 3/2012 |
| WO | WO2015097104 | A1 | 7/2015 |

OTHER PUBLICATIONS

Park et al., "A standardized bacterial taxonomy based on genome phylogeny substantially revises the tree of life", Nature Biotechnology, 2018, 36(10):996-1004. doi:10.1038/nbt.4229.*

Zhang et al., "Propagated Perturbations from a Peripheral Mutation Show Interactions Supporting WW Domain Thermostability", Structure, vol. 26, pp. 1474-1485. (Year: 2018).*

Singh et al., "Protein Engineering Approaches in the Post-Genomic Era", Current Protein Peptide Science, vol. 19, No. 1, pp. 5-15 (Year: 2018).*

Atanasova et al., Plastic Degradation by Extremophilic Bacteria, International Journal of Molecular Sciences, vol. 22, No. 11, May 25, 2021, pp. 5610: 1-19, https://doi.org/10.3390/ijms22115610.

PCT Search Report Corresponding to Application No. PCT/US2021/034848 on Aug. 5, 2021.

García-Hidalgo et al., Extracellular production of Streptomyces exfoliatus poly(3-hydroxybutyrate) depolymerase in *Rhodococcus* sp. T104: determination of optimal biocatalyst conditions, Applied Microbiology and Biotechnology, vol. 93, 2012, pp. 1975-1988, https://doi.org/10.1007/s00253-011-3527-5.

García-Hidalgo et al., Novel Extracellular PHB Depolymerase from Streptomyces ascomycinicus: PHB Copolymers Degradation in Acidic Conditions, PLOS One, vol. 8, Issue 8, 2013, pp. 1-13, https://doi.org/10.1371/journal.pone.0071699.

Hiraishi et al., Effects of Mutations in the Substrate-Binding Domain of Poly [(R)-3- Hydroxybutyrate] (PHB) Depolymerase from Ralstonia pickettii T1 on PHB Degradation, Applied and Environmental Microbiology, vol. 72, Issue 11, 2006, pp. 7331-7338, https://doi.org/10.1128/AEM.01187-06

(Continued)

*Primary Examiner* — Suzanne M Noakes
(74) *Attorney, Agent, or Firm* — Dority & Manning, P.A.

(57) ABSTRACT

The present invention relates to a method for treatment of poly hydroxy alkanoate (PHA) containing post-consumer product, the method comprising contacting a post-consumer product with a polypeptide that can catalyze degradation of the PHA, the contact taking place at a temperature at least 40° C. and in the presence of salt at a concentration of 1 M or greater. In a specific embodiment, the polypeptide is a wild-type PHA depolymerase expressed by a halophilic microorganism or a modified PHA depolymerase that includes one or more single-site mutations as compared to the wild-type PHA depolymerase. In another specific embodiment, the polypeptide comprising a modified poly hydroxy butyrate (PHB) depolymerase comprising one or more single-site mutations as compared to SEQ ID NO: 1, and the modified PHB depolymerase having a solubility of 10 mg/L or greater. The present invention also relates to a host cell transformed to express a polypeptide that catalyzes degradation of a PHA in the presence of salt at a concentration of 1 M or greater, wherein the host cell is selected from an *E. coli* cell or a halophilic microorganism.

5 Claims, 6 Drawing Sheets

Specification includes a Sequence Listing.

(56) References Cited

OTHER PUBLICATIONS

Hiraishi et al., Protein Engineering of Enzymes Involved in Bioplastic Metabolism, Protein Engineering—Technology and Application, Chapter 6, 2013, pp. 133-165, DOI: 10.5772/55552.
Hiraishi et al., Y443F mutation in the substrate-binding domain of extracellular PHB depolymerase enhances its PHB adsorption and disruption abilities, Polymer Degradation and Stability, vol. 95, Issue 8, 2010, Abstract Only, https://doi.org/10.1016/j.polymdegradstab.2010.01.022.
Shin et al., Enhancement of PHB depolymerase Activity from Alcaligenes faecalis T1 by DNA Shuffing, Korea Agricultural Science Digital Library, vol. 39, Issue 2, 2003, Abstract Only.
Search Report for U.S. Appl. No. 18/558,880, mailed on Apr. 14, 2025, 16 pages.
Abe et al: "Enzymatic and Environmental Degradation of Racemic Poly(3-hydroxybutyric acid)s with Different Stereoregularities", Macromolecules, Jan. 1, 1996 (Jan. 1, 1996).
Suzuki et al: "Biodegradability of poly(3-hydroxyalkanoate) and poly(-caprolactone) via biological carbon cycles in marine environments", Polymer Journal, Jun. 24, 1996 (Jun. 24, 1996).
Reddy et al: "Polyhydroxyalkanoates: an overview", Bioresource Technology, vol. 87, No. 2, Apr. 1, 2003 (Apr. 1, 2003), pp. 137-146.
Yin et al: "Halophiles, coming stars for industrial biotechnology", Biotechnology Advances, Elsevier Publishing, Barking, GB, Oct. 27, 2014 (Oct. 27, 2014), pp. 1433-1442.
Roohi et al: "PHB (poly-[beta]-hydroxybutyrate) and its enzymatic degradation", Polymers for Advanced Technologies, Aug. 9, 2017 (Aug. 9, 2017), pp. 30-40.

* cited by examiner

SEQUENCE LISTING

<160> NUMBER OF SEQ ID NOS: 19

<210> SEQ ID NO 1
<211> LENGTH: 355
<212> TYPE: PRT
<213> ORGANISM: Halomonas aquamarina

<400> SEQUENCE: 1

```
Met Gly Ile Ala Val His Gln Arg Arg Leu Met Ala Ala Leu Ile Leu
1               5                   10                  15

Leu Gly Ser Ala Val Ala His Ala Glu Glu Glu Ala Pro Gly Leu Pro
            20                  25                  30

Ala Leu Gly Ala Ala Asn Asp Gln Ala Ser Val Val Gly Val Ser Ser
        35                  40                  45

Gly Gly Tyr Met Ala Ser Gln Leu Ala Val Ala Trp Pro Glu Arg Phe
    50                  55                  60

Ser Gly Val Gly Met Leu Ala Ala Gly Pro Trp Gly Cys Ala Gln Gly
65                  70                  75                  80

Ala Leu Ser Leu Ala Leu Asn Gln Cys Met Met Thr Arg Arg Gly Leu
                85                  90                  95

Pro Ser Leu Asp Glu Leu Glu Gln Arg Arg Glu Arg Tyr Leu Ser Leu
            100                 105                 110

Asp Gln Val Gly Ser Gln Asp Ala Leu Ser Gln Leu Arg Ala Phe Val
        115                 120                 125

Trp His Gly Asp Ala Asp Glu Thr Val Ser Pro Ala Leu Gly Asp Leu
    130                 135                 140

Leu Ala Gln Gln Trp Gln Gly Trp Leu Glu Ser Pro Glu Gln Gln Leu
145                 150                 155                 160

Arg Tyr Val Gln Arg Ala Asn Thr Gly His Gly Trp Pro Val Ala Met
                165                 170                 175

Pro Lys Asp Ala Pro Ile Asp Pro Gln Ser Leu Gly Asp Cys Arg Asn
            180                 185                 190

Gly Gly Gly Ser His Val Leu Ala Cys Gly Glu Asp Val Ala Gly Glu
        195                 200                 205

Met Met Ala Trp Leu Tyr Pro Glu Arg Glu Thr Asn Ala Ser Glu Gly
    210                 215                 220

Glu Leu Leu Ala Phe Asp Gln Ser Asp Phe Ala Ala Lys Gly Phe Ala
225                 230                 235                 240

Asp Thr Gly Tyr Val Phe Val Pro Glu Ala Cys Glu Ala Gly Gly Cys
                245                 250                 255

Pro Val Thr Val Ala Leu His Gly Cys Gln Met Asn Ala Glu Ala Ile
            260                 265                 270

Asp Asp Thr Phe Val Arg Tyr Ser Gly Leu Asn Arg Trp Ala Ala Glu
        275                 280                 285

His Gly Gln Val Val Leu Tyr Pro Gln Ala Glu Ser Ser Met Ala Asn
    290                 295                 300

Pro Gln Ala Cys Trp Asp Trp Trp Gly Phe Ala Glu Ser Thr Trp Gln
305                 310                 315                 320

Ile Asn Pro Leu His Asp Thr Arg Asp Gly Thr Gln Thr Gln Ala Leu
                325                 330                 335

Met Ala Met Leu Asp His Leu Gln Ser Ala Thr Ala Asn Lys Ala Ala
            340                 345                 350

Thr Ala Glu
        355
```

-continued

<210> SEQ ID NO 2
<211> LENGTH: 9
<212> TYPE: PRT
<213> ORGANISM: Halomonas aquamarina

<400> SEQUENCE: 2

Ala Ala Gly Pro Trp Gly Cys Ala Gln
1               5

<210> SEQ ID NO 3
<211> LENGTH: 10
<212> TYPE: PRT
<213> ORGANISM: Halomonas aquamarina

<400> SEQUENCE: 3

Arg Ala Phe Val Trp His Gly Asp Ala Asp
1               5                   10

<210> SEQ ID NO 4
<211> LENGTH: 7
<212> TYPE: PRT
<213> ORGANISM: Halomonas aquamarina

<400> SEQUENCE: 4

Gly Gly Cys Pro Val Thr Val
1               5

<210> SEQ ID NO 5
<211> LENGTH: 332
<212> TYPE: PRT
<213> ORGANISM: Halomonas aquamarina

<400> SEQUENCE: 5

Met Glu Glu Glu Ala Pro Gly Leu Pro Ala Leu Gly Ala Ala Asn Asp
1               5                   10                  15

Gln Ala Ser Val Val Gly Val Ser Ser Gly Gly Tyr Met Ala Ser Gln
            20                  25                  30

Leu Ala Val Ala Trp Pro Glu Arg Phe Ser Gly Val Gly Met Leu Ala
        35                  40                  45

Ala Gly Pro Trp Gly Cys Ala Gln Gly Ala Leu Ser Leu Ala Leu Asn
    50                  55                  60

Gln Cys Met Met Thr Arg Arg Gly Leu Pro Ser Leu Asp Glu Leu Glu
65                  70                  75                  80

Gln Arg Arg Glu Arg Tyr Leu Ser Leu Asp Gln Val Gly Ser Gln Asp
                85                  90                  95

Ala Leu Ser Gln Leu Arg Ala Phe Val Trp His Gly Asp Ala Asp Glu
            100                 105                 110

Thr Val Ser Pro Ala Leu Gly Asp Leu Leu Ala Gln Gln Trp Gln Gly
        115                 120                 125

Trp Leu Glu Ser Pro Glu Gln Gln Leu Arg Tyr Val Gln Arg Ala Asn
    130                 135                 140

Thr Gly His Gly Trp Pro Val Ala Met Pro Lys Asp Ala Pro Ile Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Gly Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

```
Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Ala Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Gln Ser Ala Thr Ala Asn Lys Ala Ala Thr Ala Glu
                325                 330


<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met His His His His His His Gly Ser Glu Asn Leu Tyr Phe Gln Ser
1               5                   10                  15


<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Met Glu Glu Glu
1               5


<210> SEQ ID NO 8
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Glu Glu Glu Ala Pro Gly Leu Pro Ala Leu Gly Ala Ala Asn Asp
1               5                   10                  15

Gln Ala Ser Val Val Gly Val Ser Ser Gly Gly Tyr Met Ala Ser Gln
            20                  25                  30

Leu Ala Val Ala Trp Pro Glu Arg Phe Ser Gly Val Gly Met Leu Ala
        35                  40                  45

Ala Gly Pro Trp Gly Cys Ala Gln Gly Ser Leu Ser Leu Ala Leu Asn
    50                  55                  60

Gln Cys Met Met Thr Arg Arg Gly Leu Pro Ser Leu Asp Glu Leu Glu
65                  70                  75                  80
```

-continued

```
Gln Arg Arg Glu Arg Tyr Leu Ser Ser Asp Gln Val Gly Ser Gln Asp
                85                  90                  95

Ala Leu Ser Gln Leu Arg Ala Phe Val Trp His Gly Asp Ala Asp Glu
            100                 105                 110

Thr Val Ser Pro Ala Leu Gly Asp Leu Leu Ala Gln Gln Trp Gln Gly
        115                 120                 125

Trp Leu Glu Ser Pro Glu Gln Gln Leu Arg Tyr Val Gln Ser Ala Asn
    130                 135                 140

Thr Gly His Gly Trp Pro Val Ala Met Pro Lys Asp Ala Pro Ser Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Gly Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Ala Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Gln Ser Ala Thr Ala Asn Lys Ala Ala Thr Ala Glu
                325                 330
```

<210> SEQ ID NO 9
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Glu Glu Glu Ala Pro Gly Leu Pro Ala Leu Pro Tyr Ala Asn Asp
1               5                   10                  15

Gln Leu Tyr Val Val Gly Val Ser Ser Gly Gly Tyr Met Ala Leu Gln
            20                  25                  30

Leu Leu Val Ala Trp Pro Glu Arg Phe Ser Gly Val Gly Met Leu Ala
        35                  40                  45

Ala Leu Pro Trp Gly Cys Ala Gln Gly Ala Leu Ser Leu Ala Leu Asn
    50                  55                  60

Gln Cys Met Met Thr Arg Arg Gly Leu Pro Ser Leu Asp Glu Leu Glu
65                  70                  75                  80

Gln Arg Arg Glu Arg Tyr Leu Ser Leu Asp Gln Val Gly Ser Gln Asp
                85                  90                  95

Ala Leu Ser Gln Leu Arg Ile Phe Val Trp His Gly Asp Ala Asp Glu
            100                 105                 110
```

Thr Val Ser Pro Ala Leu Leu Asp Leu Leu Ala Gln Gln Trp Gln Gly
        115                 120                 125

Trp Leu Glu Ser Pro Glu Gln Gln Leu Arg Tyr Val Gln Arg Ala Asn
    130                 135                 140

Thr Gly His Gly Trp Pro Val Ala Met Pro Lys Asp Ala Pro Ile Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Trp Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Trp Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Gln Ser Ala Thr Ala Asn Lys Ala Ala Thr Ala Glu
                325                 330

<210> SEQ ID NO 10
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Glu Glu Ala Pro Gly Leu Pro Ala Leu Pro Tyr Ala Asn Asp
1               5                   10                  15

Gln Leu Tyr Val Val Gly Val Ser Ser Gly Gly Tyr Met Ala Leu Gln
            20                  25                  30

Leu Leu Val Ala Trp Pro Glu Arg Phe Ser Gly Val Gly Met Leu Ala
        35                  40                  45

Ala Leu Pro Trp Gly Cys Ala Gln Gly Ser Leu Ser Leu Ala Leu Asn
    50                  55                  60

Gln Cys Met Met Thr Arg Arg Gly Leu Pro Ser Leu Asp Glu Leu Glu
65                  70                  75                  80

Gln Arg Arg Glu Arg Tyr Leu Ser Ser Asp Gln Val Gly Ser Gln Asp
                85                  90                  95

Ala Leu Ser Gln Leu Arg Ile Phe Val Trp His Gly Asp Ala Asp Glu
            100                 105                 110

Thr Val Ser Pro Ala Leu Leu Asp Leu Leu Ala Gln Gln Trp Gln Gly
        115                 120                 125

Trp Leu Glu Ser Pro Glu Gln Gln Leu Arg Tyr Val Gln Ser Ala Asn

-continued

```
    130                 135                 140

Thr Gly His Gly Trp Pro Val Ala Met Pro Lys Asp Ala Pro Ser Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Trp Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Trp Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Gln Ser Ala Thr Ala Asn Lys Ala Ala Thr Ala Glu
                325                 330


<210> SEQ ID NO 11
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Glu Glu Ala Pro Gly Leu Pro Ala Leu Gly Ala Ala Phe Asp
1               5                   10                  15

Gln Ala Ser Val Val Gly Val Ser Ser Gly Gly Tyr Met Ala Ser Gln
            20                  25                  30

Leu Ala Val Ala Trp Pro Glu Arg Phe Ser Gly Val Gly Trp Leu Ala
        35                  40                  45

Gly Gly Pro Trp Gly Cys Ala Gln Gly Ala Leu Ser Leu Ala Leu Asn
    50                  55                  60

Gln Cys Met Met Thr Arg Arg Gly Leu Pro Ser Leu Asp Glu Leu Leu
65                  70                  75                  80

Gln Arg Leu Glu Arg Tyr Leu Ser Leu Asp Gln Val Gly Ser Leu Asp
                85                  90                  95

Ala Leu Ser Gln Leu Arg Ala Phe Val Trp His Gly Asp Ala Asp Glu
            100                 105                 110

Thr Val Ser Pro Ala Leu Gly Asp Leu Leu Ala Gln Gln Trp Gln Gly
        115                 120                 125

Trp Leu Glu Ser Pro Glu Gln Gln Leu Arg Tyr Val Ile Arg Ala Asn
    130                 135                 140

Thr Gly His Gly Trp Trp Val Ala Met Pro Lys Asp Ala Pro Ile Asp
145                 150                 155                 160
```

```
Pro Gln Ser Leu Gly Asp Cys Arg Asn Gly Gly Gly Ser His Val Leu
                165                 170                 175

Ala Cys Gly Glu Asp Val Ala Gly Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Ala Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Thr Ser Ala Thr Ala Asn Lys Ala Ala Thr Ala Glu
                325                 330
```

```
<210> SEQ ID NO 12
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Glu Glu Ala Pro Gly Leu Pro Ala Leu Gly Ala Ala Phe Asp
1               5                   10                  15

Gln Ala Ser Val Val Gly Val Ser Ser Gly Gly Tyr Met Ala Ser Gln
            20                  25                  30

Leu Ala Val Ala Trp Pro Glu Arg Phe Ser Gly Val Gly Trp Leu Ala
        35                  40                  45

Gly Gly Pro Trp Gly Cys Ala Gln Gly Ser Leu Ser Leu Ala Leu Asn
    50                  55                  60

Gln Cys Met Met Thr Arg Arg Gly Leu Pro Ser Leu Asp Glu Leu Leu
65                  70                  75                  80

Gln Arg Leu Glu Arg Tyr Leu Ser Ser Asp Gln Val Gly Ser Leu Asp
                85                  90                  95

Ala Leu Ser Gln Leu Arg Ala Phe Val Trp His Gly Asp Ala Asp Glu
            100                 105                 110

Thr Val Ser Pro Ala Leu Gly Asp Leu Leu Ala Gln Gln Trp Gln Gly
        115                 120                 125

Trp Leu Glu Ser Pro Glu Gln Gln Leu Arg Tyr Val Ile Ser Ala Asn
    130                 135                 140

Thr Gly His Gly Trp Trp Val Ala Met Pro Lys Asp Ala Pro Ser Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Gly Glu Met Met Ala Trp Leu Tyr Pro
            180                 185                 190
```

-continued

```
Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Ala Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Thr Ser Ala Thr Ala Asn Lys Ala Ala Thr Ala Glu
                325                 330


<210> SEQ ID NO 13
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Glu Glu Ala Pro Gly Leu Pro Ala Leu Pro Tyr Ala Phe Asp
1               5                   10                  15

Gln Leu Tyr Val Val Gly Val Ser Ser Gly Gly Tyr Met Ala Leu Gln
            20                  25                  30

Leu Leu Val Ala Trp Pro Glu Arg Phe Ser Gly Val Gly Trp Leu Ala
        35                  40                  45

Gly Leu Pro Trp Gly Cys Ala Gln Gly Ala Leu Ser Leu Ala Leu Asn
    50                  55                  60

Gln Cys Met Met Thr Arg Arg Gly Leu Pro Ser Leu Asp Glu Leu Leu
65                  70                  75                  80

Gln Arg Leu Glu Arg Tyr Leu Ser Leu Asp Gln Val Gly Ser Leu Asp
                85                  90                  95

Ala Leu Ser Gln Leu Arg Ile Phe Val Trp His Gly Asp Ala Asp Glu
            100                 105                 110

Thr Val Ser Pro Ala Leu Leu Asp Leu Leu Ala Gln Gln Trp Gln Gly
        115                 120                 125

Trp Leu Glu Ser Pro Glu Gln Gln Leu Arg Tyr Val Ile Arg Ala Asn
    130                 135                 140

Thr Gly His Gly Trp Trp Val Ala Met Pro Lys Asp Ala Pro Ile Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Trp Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
```

```
    210                 215                 220

Pro Glu Ala Cys Glu Ala Gly Gly Cys Pro Val Thr Val Trp Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Thr Ser Ala Thr Ala Asn Lys Ala Ala Thr Ala Glu
                325                 330


<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Asp Lys Ile Ile His Leu Thr Asp Asp Ser Phe Asp Thr Asp Val
1               5                   10                  15

Leu Lys Ala Asp Gly Ala Ile Leu Val Asp Phe Trp Ala Glu Trp Cys
            20                  25                  30

Gly Pro Cys Lys Met Ile Ala Pro Ile Leu Asp Glu Ile Ala Asp Glu
        35                  40                  45

Tyr Gln Gly Lys Leu Thr Val Ala Lys Leu Asn Ile Asp Gln Asn Pro
    50                  55                  60

Gly Thr Ala Pro Lys Tyr Gly Ile Arg Gly Ile Pro Thr Leu Leu Leu
65                  70                  75                  80

Phe Lys Asn Gly Glu Val Ala Ala Thr Lys Val Gly Ala Leu Ser Lys
                85                  90                  95

Gly Gln Leu Lys Glu Phe Leu Asp Ala Asn Leu Ala
            100                 105


<210> SEQ ID NO 15
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Glu Glu Glu Ala Pro Gly Leu Pro Ala Leu Pro Tyr Ala Phe Asp
1               5                   10                  15

Gln Leu Tyr Val Val Gly Val Ser Ser Gly Gly Tyr Met Ala Leu Gln
            20                  25                  30

Leu Leu Val Ala Trp Pro Glu Arg Phe Ser Gly Val Gly Trp Leu Ala
        35                  40                  45

Gly Leu Pro Trp Gly Cys Ala Gln Gly Ser Leu Ser Leu Ala Leu Asn
    50                  55                  60

Gln Cys Met Met Thr Arg Arg Gly Leu Pro Ser Leu Asp Glu Leu Leu
```

-continued

```
65                  70                  75                  80

Gln Arg Leu Glu Arg Tyr Leu Ser Ser Asp Gln Val Gly Ser Leu Asp
                85                  90                  95

Ala Leu Ser Gln Leu Arg Ile Phe Val Trp His Gly Asp Ala Asp Glu
            100                 105                 110

Thr Val Ser Pro Ala Leu Leu Asp Leu Leu Ala Gln Gln Trp Gln Gly
        115                 120                 125

Trp Leu Glu Ser Pro Glu Gln Gln Leu Arg Tyr Val Ile Ser Ala Asn
    130                 135                 140

Thr Gly His Gly Trp Trp Val Ala Met Pro Lys Asp Ala Pro Ser Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Trp Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Trp Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Thr Ser Ala Thr Ala Asn Lys Ala Ala Thr Ala Glu
                325                 330
```

<210> SEQ ID NO 16
<211> LENGTH: 332
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(12)
<223> OTHER INFORMATION: P, L, F, W or N
<220> FEATURE:
<221> NAME/KEY: MOD_RES
<222> LOCATION: (13)..(13)
<223> OTHER INFORMATION: Y, W, I, F, L or V
<220> FEATURE:
<221> NAME/KEY: MOD_RES
<222> LOCATION: (15)..(15)
<223> OTHER INFORMATION: F, L or V
<220> FEATURE:
<221> NAME/KEY: MOD_RES
<222> LOCATION: (17)..(17)
<223> OTHER INFORMATION: L, F, I, W, V, M, Y, C or T
<220> FEATURE:
<221> NAME/KEY: MOD_RES
<222> LOCATION: (18)..(18)
<223> OTHER INFORMATION: Y, W or F
<220> FEATURE:

<221> NAME/KEY: MOD_RES
<222> LOCATION: (31)..(31)
<223> OTHER INFORMATION: L, I, W, F, V, M or Y
<220> FEATURE:
<221> NAME/KEY: MOD_RES
<222> LOCATION: (34)..(34)
<223> OTHER INFORMATION: L, F, I, W, M or H
<220> FEATURE:
<221> NAME/KEY: MOD_RES
<222> LOCATION: (49)..(49)
<223> OTHER INFORMATION: G, L, F or W
<220> FEATURE:
<221> NAME/KEY: MOD_RES
<222> LOCATION: (50)..(50)
<223> OTHER INFORMATION: L, F, W or L
<220> FEATURE:
<221> NAME/KEY: MOD_RES
<222> LOCATION: (80)..(80)
<223> OTHER INFORMATION: L, W, V or M
<220> FEATURE:
<221> NAME/KEY: MOD_RES
<222> LOCATION: (83)..(83)
<223> OTHER INFORMATION: L, F, I, V, T, M, A or W
<220> FEATURE:
<221> NAME/KEY: MOD_RES
<222> LOCATION: (95)..(95)
<223> OTHER INFORMATION: L, I or W
<220> FEATURE:
<221> NAME/KEY: MOD_RES
<222> LOCATION: (103)..(103)
<223> OTHER INFORMATION: I, Y, L, F, W, V or M
<220> FEATURE:
<221> NAME/KEY: MOD_RES
<222> LOCATION: (119)..(119)
<223> OTHER INFORMATION: L, F, W, I, M, Y, T, V or C
<220> FEATURE:
<221> NAME/KEY: MOD_RES
<222> LOCATION: (141)..(141)
<223> OTHER INFORMATION: I, Y, W, L, V or F
<220> FEATURE:
<221> NAME/KEY: MOD_RES
<222> LOCATION: (184)..(184)
<223> OTHER INFORMATION: W, L or F
<220> FEATURE:
<221> NAME/KEY: MOD_RES
<222> LOCATION: (238)..(238)
<223> OTHER INFORMATION: W, F or Y
<220> FEATURE:
<221> NAME/KEY: MOD_RES
<222> LOCATION: (321)..(321)
<223> OTHER INFORMATION: T, V, I, L, F or M

<400> SEQUENCE: 16

```
Met Glu Glu Glu Ala Pro Gly Leu Pro Ala Leu Xaa Xaa Ala Xaa Asp
1               5                   10                  15

Xaa Xaa Ser Val Val Gly Val Ser Ser Gly Gly Tyr Met Ala Xaa Gln
            20                  25                  30

Leu Xaa Val Ala Trp Pro Glu Arg Phe Ser Gly Val Gly Trp Leu Ala
        35                  40                  45

Xaa Xaa Pro Trp Gly Cys Ala Gln Gly Ala Leu Ser Leu Ala Leu Asn
    50                  55                  60

Gln Cys Met Met Thr Arg Arg Gly Leu Pro Ser Leu Asp Glu Leu Xaa
65                  70                  75                  80

Gln Arg Xaa Glu Arg Tyr Leu Ser Leu Asp Gln Val Gly Ser Xaa Asp
                85                  90                  95

Ala Leu Ser Gln Leu Arg Xaa Phe Val Trp His Gly Asp Ala Asp Glu
            100                 105                 110

Thr Val Ser Pro Ala Leu Xaa Asp Leu Leu Ala Gln Gln Trp Gln Gly
        115                 120                 125

Trp Leu Glu Ser Pro Glu Gln Gln Leu Arg Tyr Val Xaa Ile Ala Asn
```

-continued

```
    130                 135                 140

Thr Gly His Gly Trp Trp Val Ala Met Pro Lys Asp Ala Pro Ile Asp
145                 150                 155                 160

Pro Gln Ser Leu Gly Asp Cys Arg Asn Gly Gly Gly Ser His Val Leu
                165                 170                 175

Ala Cys Gly Glu Asp Val Ala Xaa Glu Met Met Ala Trp Leu Tyr Pro
            180                 185                 190

Glu Arg Glu Thr Asn Ala Ser Glu Gly Glu Leu Leu Ala Phe Asp Gln
        195                 200                 205

Ser Asp Phe Ala Ala Lys Gly Phe Ala Asp Thr Gly Tyr Val Phe Val
    210                 215                 220

Pro Glu Ala Cys Glu Ala Gly Gly Cys Pro Val Thr Val Xaa Leu His
225                 230                 235                 240

Gly Cys Gln Met Asn Ala Glu Ala Ile Asp Asp Thr Phe Val Arg Tyr
                245                 250                 255

Ser Gly Leu Asn Arg Trp Ala Ala Glu His Gly Gln Val Val Leu Tyr
            260                 265                 270

Pro Gln Ala Glu Ser Ser Met Ala Asn Pro Gln Ala Cys Trp Asp Trp
        275                 280                 285

Trp Gly Phe Ala Glu Ser Thr Trp Gln Ile Asn Pro Leu His Asp Thr
    290                 295                 300

Arg Asp Gly Thr Gln Thr Gln Ala Leu Met Ala Met Leu Asp His Leu
305                 310                 315                 320

Xaa Ser Ala Thr Ala Asn Lys Ala Ala Thr Ala Glu
                325                 330


<210> SEQ ID NO 17
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Y, W, I or F
<220> FEATURE:
<221> NAME/KEY: MOD_RES
<222> LOCATION: (18)..(18)
<223> OTHER INFORMATION: L, F, I or W
<220> FEATURE:
<221> NAME/KEY: MOD_RES
<222> LOCATION: (19)..(19)
<223> OTHER INFORMATION: Y, W or L
<220> FEATURE:
<221> NAME/KEY: MOD_RES
<222> LOCATION: (83)..(83)
<223> OTHER INFORMATION: L, F, I or V
<220> FEATURE:
<221> NAME/KEY: MOD_RES
<222> LOCATION: (119)..(119)
<223> OTHER INFORMATION: L or F
<220> FEATURE:
<221> NAME/KEY: MOD_RES
<222> LOCATION: (322)..(322)
<223> OTHER INFORMATION: T, V, I or L

<400> SEQUENCE: 17

Met Glu Glu Glu Ala Pro Gly Leu Pro Ala Leu Gly Xaa Ala Asn Asp
1               5                   10                  15

Gln Xaa Xaa Val Val Gly Val Ser Ser Gly Gly Tyr Met Ala Leu Gln
            20                  25                  30
```

-continued

```
Leu Leu Val Ala Trp Pro Glu Arg Phe Ser Gly Val Gly Met Leu Ala
        35                  40                  45

Gly Gly Pro Trp Gly Cys Ala Gln Gly Ala Leu Ser Leu Ala Leu Asn
    50                  55                  60

Gln Cys Met Met Thr Arg Arg Gly Leu Pro Ser Leu Asp Glu Leu Glu
65                  70                  75                  80

Gln Arg Xaa Glu Arg Tyr Leu Ser Leu Asp Gln Val Gly Ser Gln Asp
                85                  90                  95

Ala Leu Ser Gln Leu Arg Ile Phe Val Trp His Gly Asp Ala Asp Glu
            100                 105                 110

Thr Val Ser Pro Ala Leu Xaa Asp Leu Leu Ala Gln Gln Trp Gln Gly
        115                 120                 125

Trp Leu Glu Ser Pro Glu Gln Gln Leu Arg Tyr Val Ile Gln Arg Ala
    130                 135                 140

Asn Thr Gly His Gly Trp Pro Val Ala Met Pro Lys Asp Ala Pro Ile
145                 150                 155                 160

Asp Pro Gln Ser Leu Gly Asp Cys Arg Asn Gly Gly Gly Ser His Val
                165                 170                 175

Leu Ala Cys Gly Glu Asp Val Ala Trp Glu Met Met Ala Trp Leu Tyr
            180                 185                 190

Pro Glu Arg Glu Thr Asn Ala Ser Glu Gly Glu Leu Leu Ala Phe Asp
        195                 200                 205

Gln Ser Asp Phe Ala Ala Lys Gly Phe Ala Asp Thr Gly Tyr Val Phe
    210                 215                 220

Val Pro Glu Ala Cys Glu Ala Gly Gly Cys Pro Val Thr Val Ala Leu
225                 230                 235                 240

His Gly Cys Gln Met Asn Ala Glu Ala Ile Asp Asp Thr Phe Val Arg
                245                 250                 255

Tyr Ser Gly Leu Asn Arg Trp Ala Ala Glu His Gly Gln Val Val Leu
            260                 265                 270

Tyr Pro Gln Ala Glu Ser Ser Met Ala Asn Pro Gln Ala Cys Trp Asp
        275                 280                 285

Trp Trp Gly Phe Ala Glu Ser Thr Trp Gln Ile Asn Pro Leu His Asp
    290                 295                 300

Thr Arg Asp Gly Thr Gln Thr Gln Ala Leu Met Ala Met Leu Asp His
305                 310                 315                 320

Leu Xaa Ser Ala Thr Ala Asn Lys Ala Ala Thr Ala Glu
                325                 330
```

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 18

```
His His His His His His
1               5
```

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic peptide -continued

```
<400> SEQUENCE: 19

Gly Ser Gly Ser Gly Ser
1               5
```

OPTIMIZATION OF A HALOPHILIC PHB DEPOLYMERASE FOR INDUSTRIAL APPLICATIONS

RELATED APPLICATIONS

The present application is the national stage entry of International Patent Application No. PCT/US2021/034848 having a filing date of May 28, 2021, which is incorporated herein in its entirety by reference thereto.

SEQUENCE LISTING

This application contains a Sequence Listing which has been submitted electronically in ASCII format and is hereby incorporated by reference in its entirety. Said ASCII copy, created on Oct. 30, 2023, is named KCX-2016-PCTUS SL.txt and is 37,049 bytes in size.

BACKGROUND

It has been estimated that over 300,000,000 metric tons of petroleum-based polymers are being produced each year with global production continuing to increase. A significant portion of these polymers are used to produce single-use products, such as plastic drinking bottles, straws, packaging, and personal care products. Most of these plastic products are discarded and do not enter the recycle stream. As the worldwide single-use plastic epidemic worsens, it becomes paramount to identify fully renewable plastics and to develop methods and materials that provide for industrial processing of renewable plastics.

Biodegradable polymers produced from renewable resources (also termed "biopolymers") hold great promise for reducing the global accumulation of petroleum-based plastics in the environment. One such class of biopolymers are the polyhydroxyalkanoates (PHA). Much work has been accomplished on the PHA family, most notably the polyhydroxybutyrate (PHB) polymers including poly-3-hydroxybutyrate (P3HB), poly-4-hydroxybutyrate (P4HB), polyhydroxyvalerate (PHV), polyhydroxyhexanoate (PHH), polyhydroxyoctanoate (PHO) and their copolymers. Of particular advantage, PHA exhibit thermoplastic properties that are very similar to some petroleum-based polymers and thus represent viable replacements for petroleum-based polymers such as polypropylene and polyethylene.

PHA are naturally produced across many bacterial, fungal, and archaeal lineages, including *Azotobacter, Ralstonia, Burkholderia, Protomonas, Bacillus*, and *Schlegelella*, for use as an energy sink. Production of PHA polymers involves a three-step enzymatic mechanism that begins with acetyl coenzyme A. In forming PHB, the first step is catalysis of acetyl-CoA by PhaA (a β-ketothiolase) to form β-ketoacyl-CoA. This in turn is converted in a NADP-dependent reaction into R-3-hydroxyacyl-CoA by the PhaB enzyme (a β-ketoacyl-CoA reductase). The final step, catalyzed by PhaC (a PHB synthase), is the polymerization of R-3-hydroxyacyl-CoA into PHB.

In nature, to retrieve the energy stored in the polymer, biodegradation is accomplished by a PHA depolymerase (PHADase). Unfortunately, natural PHADase are generally not conducive to industrial processes, e.g., post-consumer recycle processes, as an enzyme that is used for any bio-industrial process must have several characteristics that typical PHADase lack in sufficient level so as to be industrially useful. To be broadly useful, an enzyme for use in an industrial process should be thermodynamically and/or thermally stable in order to be long-lived in the process. An enzyme should also be as kinetically fast as possible so that a maximum amount of substrate is converted to product in a minimal amount of time. It must also be fully active in the environmental conditions of the industrial process. For example, in a process directed to processing of soiled PHB-containing personal care products (e.g., diaper, feminine pad, incontinence garment, etc.), the enzyme must be able to function in an environment that is contaminated with feces, urine, menstrual fluid, etc. Ideally, the enzyme should be functional in a processing environment that is designed to neutralize contaminants that may be present in used consumer products (e.g., mesophilic bacteria).

A need exists for materials and methods that can increase the use of biopolymers in consumer products and industrial processes. Industrial processing materials and methods that can be used in processing biopolymers from post-consumer personal care products, for instance in a recycling process, would be of great benefit in the art.

SUMMARY

In general, the present disclosure is directed to catalysts for industrial degradation of PHA polymers and systems incorporating the catalysts. PHA polymers for degradation by the catalysts can be components of post-consumer products, such as post-consumer personal care products. Currently, a significant portion of post-consumer products including, without limitation, packaging, straws, cups, bottles, shopping bags, eating utensils, trays, and personal care products such as personal care garments (e.g., diapers, child training pants, disposable swim pants, feminine hygiene products, adult incontinence products), tampon dispensers, medical supplies, etc., are made from petroleum-based polymers. Significant efforts are currently underway to incorporate biopolymers such as PHA into such products as well as to improve and encourage the recycling of the biopolymers. The present disclosure is directed to improved catalysts and systems that target biopolymers in high salt content, high temperature industrial processes for simultaneous degradation and decontamination.

In one aspect, disclosed are methods for treating post-consumer products that include a PHA. For instance, a method can include contacting a post-consumer product, e.g., a post-consumer personal care product, with a polypeptide that catalyzes degradation of the PHA. The contact can take place at contact conditions that include a salt content of about 1 M or greater and a temperature of about 40° C. or greater. The catalytic polypeptide can be particularly suited for use in an industrial process, i.e., a halophilic catalytic polypeptide that exhibits excellent solubility, thermal, and kinetic characteristics. In one embodiment, the polypeptide can include a PHB depolymerase (PHBDase) produced from a microorganism that is both halophilic and thermophilic. For instance, the process can include contacting the post-consumer product with a natural halophilic and thermophilic PHBDase and/or contacting the post-consumer care product with a microorganism that can produce a polypeptide that includes the PHBDase. In one embodiment, the process can include contacting a post-consumer product with a polypeptide that includes a modified PHBDase that incorporates one or more single-site mutations as compared to a wild-type PHBDase as produced from a halophile and/or contacting the post-consumer product with a transformed microorganism that can produce the modified PHB-Dase.

In one aspect, disclosed is a modified PHADase and a transformed cell that expresses the modified PHADase. A modified PHADase as described can exhibit excellent solubility, stability and enzymatic activity at high salt content and high temperature processing conditions, e.g., a solubility in a buffer system or aqueous system of about 10 mg/L or greater. A modified PHADase can be based upon a wild-type halophilic PHBDase and can include one or more single-site mutations as compared to the wild-type enzyme. In one aspect, mutations can be in regions that are not highly conserved among halophile PHBDase enzymes so as to provide a modified enzyme that exhibits desired catalytic activity with improved solubility, stability, thermal, and/or kinetic characteristics as compared to a wild-type enzyme.

In one aspect, a modified PHBDase is disclosed that can include one or more single-site mutations as compared to SEQ ID NO: 1, which describes a wild-type PHBDase produced by the thermophile *Halomona aquamarina*. For instance, a modified PHBDase can include a mutation at one or more of positions 12, 13, 15, 18, 19, 31, 34, 46, 49, 50, 58, 80, 83, 89, 95, 103, 119, 141, 142, 150, 159, 184, 238, or 321 of SEQ ID NO: 5.

In one aspect, disclosed is a polypeptide that includes SEQ ID NO: 8, SEQ ID NO: 9, SEQ ID NO: 10, SEQ ID NO; 11, SEQ ID NO: 12, SEQ ID NO: 13, SEQ ID NO; 15, SEQ ID NO: 16, or SEQ ID NO: 17.

BRIEF DESCRIPTION OF THE DRAWINGS

A full and enabling disclosure of the present subject matter, including the best mode thereof to one of ordinary skill in the art, is set forth more particularly in the remainder of the specification, including reference to the accompanying figures in which.

Figure 1:
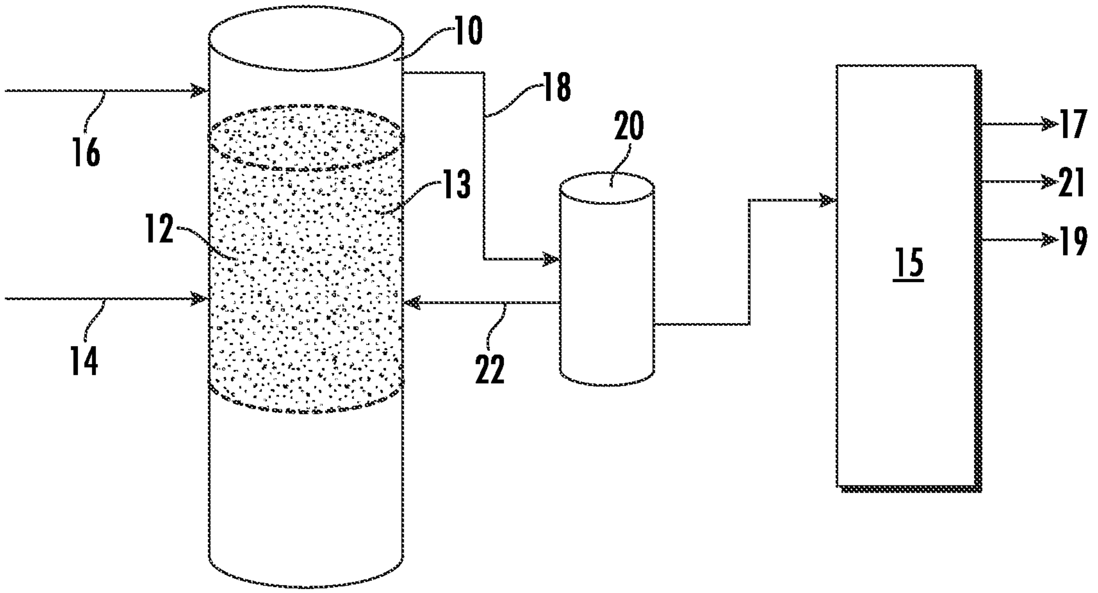
FIG. 1 schematically illustrates a bioreactor as may be utilized according to disclosed methods.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In order to reduce and eliminate polymer waste, not only is it necessary to replace petroleum-based polymers with biopolymers but it is also required to improved post-consumer processing of these polymers. Significant research is currently underway to improve mass processing of biopolymers. Such polymers are well-suited to producing all different types of single-use products, such as drink bottles, containers, packaging, and the like. In addition, those skilled in the art have proposed replacing petroleum-based polymers found in disposable personal care products, such as incontinence products with biopolymers, such as PHA polymers. The use of biopolymers to replace petroleum-based polymers will make significant strides in creating a sustainable economy.

Most plastic single-use products, such as packaging, straws, cups, bottles, shopping bags, eating utensils, trays, personal care products, etc. are buried in landfills after use. Even if made from biopolymers, these materials will still require a significant amount of time to degrade and often are combined with other, less degradable materials. Moreover, single-use products such as personal care products can be contaminated with human waste, e.g., feces, urine, blood, menstrual fluid, etc. at disposal. In order to further improve the sustainability equation, the present disclosure is directed to a method and system for industrial processing of biopolymers of post-consumer products, and in one particular embodiment, of post-consumer personal care products.

In this regard, the present disclosure is generally directed to industrial processing systems and halophilic enzymes that can be incorporated into the systems for simultaneous degradation and decontamination of biopolymers, and in one particular aspect, of PHAs. In one aspect, the enzymes are wild-type enzymes that can be incorporated into a relatively high-temperature, high-salt content industrial process. In other aspects, modified enzymes are described that can exhibit improved characteristics over the wild-type halophilic enzymes when incorporated into an industrial degradation/decontamination process. The materials, methods, and systems of the present disclosure are particularly directed to rapidly degrading and decontaminating used products containing PHA polymers using wild-type and/or modified depolymerase enzymes.

A system as disclosed herein can incorporate a bioreactor within which a decontamination and depolymerization operation can be carried out. One embodiment of a bioreactor system is schematically illustrated in FIG. 1. A bioreactor 10 can generally be formed of a material that can contain the enzymes, reactants, and products at the desired reaction conditions. For instance, a bioreactor can include stainless steel, borosilicate glass, Teflon® and other nonreactive temperature insensitive composite polymers, and so forth.

The bioreactor 10 can include a reaction zone 12, which can provide a contact area between an enzyme and a biopolymer for a period of time at a temperature and salt content to encourage degradation and decontamination of the biopolymer. To encourage both decontamination and biodegradation activity, the reaction zone 12 can include a catalytic polypeptide (e.g., an enzyme) and/or a microorganism that expresses a polypeptide that catalyzes the degradation of a biopolymer in a relatively high salt content environment. For instance, an enzyme and/or a microorganism that expresses an enzyme can be fed to a reactor 10 via an inlet stream 14, can be previously retained within a bed 13 within the reactor 10 that defines the reaction zone 12, or any combination thereof. The inlet stream 14 can also be utilized to provide salt continuously or periodically to the reaction zone 12 such that the salt content of the reaction zone 12 can be maintained at a concentration of, e.g., about 1 M or greater, about 1.5 M or greater, or about 2 M or greater in some embodiments.

To further encourage decontamination activity, for instance destruction of mesophilic bacteria as may be present in post-consumer personal care products, the bioreactor 10 can be capable of maintaining a temperature in the reaction zone 12 of about 40° C. or greater, about 45° C. or greater, about 50° C. or greater, or about 55° C. or greater in some embodiments, for instance from about 40° C. to about 80° C., or from about 45° ° C. to about 75° C. in some embodiments. To maintain desired temperatures, a bioreactor 10 can include heating elements, for instance can be jacketed with water or steam jackets (not shown in FIG. 1), to maintain desired temperature to be maintained in the reaction zone 12.

Enzymes for use in a system can encompass those that can provide catalytic activity at the temperatures and high salt content of the reaction zone 12. In one embodiment, an enzyme can be a naturally occurring, i.e., wild-type, halophilic and thermophilic enzyme expressed by a microorganism, and as such, capable of providing the desired functionality at the desired high-salt content and high-temperatures of a reaction zone 12. In one aspect, an enzyme can be a PHADase, and in one particular aspect, can be a PHBDase.

Among the PHADase, multi-domain PHBDase have been extensively examined. Multi-domain PHBDase generally have a domain structure including a catalytic domain (CD) at an N-terminus, a substrate-binding domain (SBD) at a C-terminus, and a linker region connecting the two domains, however, the multi-domain structure is not universal, and depolymerases have also emerged as single-domain PHBDase. Genetic analysis also shows that PHBDase can contain a lipase box pentapeptide as an active residue, indicating that these enzymes are one of the serine hydrolases. The enzymatic degradation of PHB is believed to proceed via a two-step reaction including a first step, in which the PHBDase approaches and adheres to the PHB surface followed by hydrolysis of the polymer chain.

There are a number of halophilic microorganisms known to express PHADase capable of catalytic activity at high salt content and relatively high temperature encompassed in the present disclosure, either as the wild-type enzyme or through one or more single-site mutations to improve one or more desirable characteristics of the wild-type enzyme. For instance, and without limitation, halophilic microorganisms of the genus *Halomonas* (e.g., *H. campaniensis, H. aquamarina, H. boliviensis, H. alkaliphila, H. siliphila, H. qiliaojingensis, H. heilongjiangensis, H. xinjiangensis, H. oriensis*), Haloferex (e.g., *H. mediterranei*), *Bacillus* (e.g., *B. megaterium, B. cereus*), *Halobacillus* (e.g., *H. hunanensis*), *Marinobacter* (e.g., *M. salaries, M. aromaticivorans, M. salicampi*), *Paracoccus, Rosevivax, Shewanella* (e.g., *S. vesiculosa, S. khirikhana*), and *Yangia* are understood to express PHADase in salinity concentrations, e.g., up to about 30% w/v NaCl, and may be utilized to provide a catalytic polypeptide as may be incorporated in an industrial system as described.

In one aspect, disclosed is a modified halophilic enzyme and a cell that expresses a modified halophilic enzyme that can provide desired catalytic activity in an industrial process. For instance, a modified enzyme can be derived from a wild-type halophilic PHADase and can include one or more single-site mutations that can improve one or more characteristics of a process. For instance, one or more single-site mutations to a wild-type halophilic PHADase can improve one or more of: Solubility of the polypeptide, which can increase the activity of an enzyme in an industrial process; stability of the polypeptide, which can increase the functional lifetime of an enzyme in an industrial process; kinetic characteristics of the polypeptide, which can increase the degradation rate of a polymer in an industrial process; and/or can thermal stability/thermodynamic characteristics of the polypeptide, which can increase the optimum temperature of operation of the polypeptide and/or increase the functional lifetime of the polypeptide in an industrial process. Beneficially, single-site mutations as described can provide such improvements to a wild-type enzyme when utilized in the presence of post-consumer personal care product contaminants including, without limitation, blood, menses, urine, feces, etc.

In one embodiment, single-site mutation of a wild-type enzyme can include replacement of one amino acid residue with another that is biologically and/or chemically similar, which is generally known as a conservative substitution, and that can improve stability, kinetics, or some other aspect of the modified enzyme. For example, a conservative substitution could include replacing one hydrophobic residue (A, L, G, W, F, I, P, V) for another, one hydrophilic residue (Q, S, T, M, H, Y) for another, one positive residue (R, K) for another, one negative residue (E, D) for another, etc. Amino acids are represented herein according to standard single-letter or three-letter notation, as is generally known in the art and described in Table 1, below.

TABLE 1

| Amino acid | 3-letter code | 1-letter code | Amino acid | 3-letter code | 1-letter code |
|---|---|---|---|---|---|
| Alanine | Ala | A | Arginine | Arg | R |
| Asparagine | Asn | N | Aspartate | Asp | D |
| Cysteine | Cys | C | Glutamine | Gln | Q |
| Glycine | Gly | G | Glutamic Acid | Glu | E |
| Histidine | His | H | Isoleucine | Ile | I |
| Leucine | Leu | L | Lysine | Lys | K |
| Methionine | Met | M | Phenylalanine | Phe | F |
| Proline | Pro | P | Serine | Ser | S |
| Threonine | Thr | T | Tryptophan | Trp | W |
| Tyrosine | Tyr | Y | Valine | Val | V |

In one embodiment, a wild-type enzyme can be modified to include one or more single-site mutations that can increase the solubility and/or stability of a protein. For instance, this can be accomplished by increasing the number of noncovalent molecular interactions within the enzyme (e.g., increasing the number of hydrogen bonds between protein side chains) or by filling internal cavities of an enzyme. An approach that encompasses mutations that fill internal cavities of an enzyme can be straightforward as it can be performed manually by visually inspecting the 3D enzyme structure, identifying cavities/voids, and mutating residues within the void until a substitution is found that maximally fills the void and is tolerated by surrounding residues.

Examples of single-site mutations that can fill internal cavities of an enzyme can include replacing an amino acid having a relatively small side chain (e.g., V, K, A, D, E, S, G) with an amino acid having a larger side chain (e.g., P, L, W, Y, I). In one embodiment, single-site mutations that can improve stability of an enzyme can include replacement of one or more of N, M, A, E, R, Q, P with an amino acid selected from F, W, G, L, I, W, T. In another embodiment, single-site mutations that can alter surface charge and/or hydrophobicity of an enzyme can be carried out that can improve solubility and stability, for instance replacement of one or more of A, L, R, I with a serine can improve industrial desirability of a modified enzyme as compared to a wild-type enzyme on which it is based.

In one embodiment, the change in stability of a modified enzyme as compared to a wild-type enzyme from which it was derived can be described by its Gibbs free energy value, or ΔG. Although ΔG is a single value, it can be deconstructed by methods known in the art to the free energy per residue in an ensemble calculation that approximates the contribution of a single amino acid to the overall free energy. While modified enzymes described herein can exhibit an increase in stability as compared to the wild-type enzyme, it should be understood that this is not a requirement of a modified enzyme. For instance, in some embodiments, a modified enzyme as described can be less stable than the wild-type, which can provide for an increased biopolymer degradation rate.

In one embodiment, a single-site mutation of a modified enzyme can have a ΔΔG value at that site (defined as the difference between the wild-type single site ΔG ($\Delta G_{WT}$) and the mutation single site ΔG ($\Delta G_{MUT}$) of about 1 kcal/mol or greater, about 1.5 kcal/mol or greater, or about 2 kcal/mol or greater in some embodiments. For instance, all single-site mutations of a modified enzyme can have a ΔΔG value that is about 1 kcal/mol or greater, about 1.5 kcal/mol or greater, or about 2 kcal/mol or greater, in some embodiments.

In one embodiment, the solubility of a modified enzyme, defined herein as the solubility of an enzyme in a buffer system, can be about 10 mg/L or greater, such as about 12 mg/L or greater, such as about 15 mg/L or greater, such as about 20 mg/L or greater, such as about 30 mg/L or greater, such as about 50 mg/L or greater, for instance from about 10 mg/L to about 50 mg/L or even higher in some embodiments.

In one embodiment the optimum temperature ($T_{opt}$) of a modified enzyme, defined herein as the temperature at which an enzyme is most active (i.e., the highest rate of the biological reaction that it catalyzes), can be about 5° C. or greater than the $T_{opt}$ of the wild-type enzyme on which the modified enzyme is based. For instance, when considering formation of a modified a *H. aquamarina*-based modified PHBDase, a modified enzyme can have a $T_{opt}$ of about 45° C. or greater, such as about 50° C. or greater, such as about 55° C. or greater, for instance from about 45° C. to about 60° C. in some embodiments.

In one embodiment, the specificity of a modified enzyme, defined herein as the ratio of the catalytic rate constant ($k_{cat}$) to the Michaelis constant ($K_m$) can be about 0.30 $s^{-1}$ $\mu M^{-1}$ or higher, such as about 0.31 $s^{-1}$ $\mu M^{-1}$ or higher, such as about 0.33 $s^{-1}$ $\mu M_{-1}$ or higher, for instance from about 0.30 $s^{-1}$ $\mu M_{-1}$ to about 0.40 $s^{-1}$ $\mu M^{-1}$ in some embodiments.

In one embodiment, a modified enzyme as may be utilized in an industrial process can be derived from a wild-type *H. aquamarina* PHBDase. For instance, a modified enzyme can be derived from SEQ ID NO: 1, which describes an amino acid sequence of an *H. aquamarina* PHBDase that is known in the art (GenBank Accession No. WP_089674669.1) or from SEQ ID NO: 5, which is the *H. aquamarina* PHBDase absent the leading 24 amino acid signal sequence of SEQ ID NO: 1 and including an initial methionine cloning artifact.

In general, a modified enzyme can retain active site fragments of a wild-type enzyme to ensure continued functionality (e.g., substrate binding domain, catalytic domain, etc.). For instance, and without wishing to be bound to any particular theory, when considering a modified enzyme derived from the *H. aquamarina* PHBDase, the modified enzyme can retain SEQ ID NO: 2, SEQ ID NO: 3, and SEQ ID NO; 4 without mutation, which are believed to describe active site fragments of the *H. aquamarina* PHBDase. In some embodiments, such active site fragments can be conserved across species and/or genera.

In one embodiment, a modified enzyme can include one or more single-site mutations as compared to a wild-type PHBDase enzyme described by SEQ ID NO: 5. For instance, a modified enzyme can include single-site mutations at one or more of positions 12, 13, 15, 18, 19, 31, 34, 46, 49, 50, 58, 80, 83, 89, 95, 103, 119, 141, 142, 150, 159, 184, 238, or 321 of SEQ ID NO: 5.

In one embodiment, a modified enzyme can include single-site mutations at one or more of positions 58, 89, 142, and 159 of SEQ ID NO: 5. For instance, SEQ ID NO: 5 can be modified to include one or more of A58S, L89S, R142S and I159S mutations. For instance, a modified enzyme can include all of these mutations to provide a modified enzyme described by SEQ ID NO: 8. As described further in the Examples section below, this particular modified enzyme includes 4 surface charge mutations. The modified enzyme thus formed exhibits significant increase in solubility as compared to the wild-type enzyme on which it is based.

In one embodiment, a modified enzyme can include single-site mutations at one or more of positions 12, 13, 18, 19, 31, 34, 50, 103, 119, 184, and 238 of SEQ ID NO: 5. For instance, SEQ ID NO: 5 can be modified to include one or more of G12P, A13Y, A18L, S19Y, S31L, A34L, G50L, A103I, G119L, G184W, and A238W. For instance, a modified enzyme can include all of these mutations to provide a modified enzyme as described by SEQ ID NO: 9.

In one embodiment, a modified enzyme can include single-site mutations at one or more of positions 12, 13, 18, 19, 31, 34, 50, 58, 89, 103, 119, 142, 159, 184, and 238 of SEQ ID NO: 5. For instance, SEQ ID NO: 5 can be modified to include one or more of G12P, A13Y, A18L, S19Y, S31L, A34L, G50L, A58S, L89S, A103I, G119L, R142S, I159S G184W, and A238W. For instance, a modified enzyme can include all of these mutations to provide a modified enzyme as described by SEQ ID NO: 10. As described further in the examples section, below, this particular modified enzyme includes 15 single-site mutations as compared to the wild-type enzyme. This modified enzyme can exhibit improved solubility, specificity, and thermal parameters as compared to the wild-type enzyme.

In one embodiment, a modified enzyme can include single-site mutations at one or more of positions 15, 46, 49, 80, 83, 95, 141, 150, AND 321 of SEQ ID NO: 5. For instance, a modified enzyme can include one or more of N15F, M46W, A49G, E80L, R83L, Q95L, Q141I, P150W, and Q321T. For instance, a modified enzyme can include one of these mutations at each of these sites as described by SEQ ID NO: 11.

In one embodiment, a modified enzyme can include single-site mutations at one or more of positions 15, 46, 49, 58, 80, 83, 89, 95, 141, 142, 150, 159, and 321 of SEQ ID NO: 5. For instance, a modified enzyme can include one or more of N15F, M46W, A49G, A58S, E80L, L89S, R83L, Q95L, Q141I, R142S, P150W, I159S, and Q321T. For instance, a modified enzyme can include one of these mutations at each of these sites as described by SEQ ID NO: 12. As described further in the Examples section below, this particular modified enzyme includes 13 single-site mutations as compared to the wild-type enzyme. This modified enzyme can exhibit improved solubility, specificity and thermal parameters as compared to the wild-type enzyme.

In one embodiment, a modified enzyme can include single-site mutations at one or more of positions 12, 13, 15, 18, 19, 31, 34, 46, 49, 50, 80, 83, 95, 103, 119, 141, 150, 184, 238, and 321 of SEQ ID NO: 5. For instance, a modified enzyme can include one or more of G12P, A13Y, N15F, A18L, S19Y, S31L, A34L, M46W, A49G, G50L, E80L, R83L, Q95L, A103I, G119L, Q141I, P150W, G184W, A238W, and Q321T. For instance, a modified enzyme can include one of these mutations at each of these sites as described by SEQ ID NO: 13.

In one embodiment, a modified enzyme can be described by SEQ ID NO: 15, which includes the following single-site mutations as compared to SEQ ID NO: 5: G12P, A13Y, N15F, A18L, S19Y, S31L, A34L, M46W, A49G, G50L, A58S, E80L, R83L, L89S, Q95L, A103I, G119L, Q141I, R142, S, P150W, 1159S, G184W, A238W, and Q321T.

In one embodiment, a modified enzyme can include single-site mutations at one or more of positions 12, 13, 15, 18, 19, 31, 34, 46, 49, 50, 58, 80, 83, 95, 103, 119, 141, 142, 150, 184, 238, or 321 as compared to SEQ ID NO: 5, in which each single-site mutation has a ΔΔG value of about 1.0 kcal/mol or greater. For instance, a modified enzyme can include one or more of the following single-site mutations: one of G12P, G12L, G12F, G12W, G12N; one of A13Y, A13W, A13I, A13F, A13L, A13V; one of N15F, N15L, N15V; one of A18L, A18F, A18I, A18W, A18V, A18M, A18Y, A18C, A18T; one of S19Y, S19W, S19F; one of S31L, S31I, S31W, S31F, S31V, S31M, S31Y; one of A34L, A34F, A341, A34W, A34M, A34H; M46W; one of A49G, A49L, A49F, A49W; one of G50L, G50F, G50W; A58L; one of E80L, E80W, E80V, E80M; one of R83L, R83F, R83I, R83V, R83T, R83M, R83A, R83W; one of Q95L, Q951, Q95W; one of A103I, A103Y, A103L, A103F, A103W, A103V, Q103M; one of G119L, G119F, G119W, G119I, G119M, G119Y, G119T, G119V, G119C; one of Q141I, Q141Y, Q141W, Q141L, Q141V, Q141F; R142I; P150W; one of G184W, G184L, G184F; one of A238W, A238F, A238Y; one of Q321T, Q321V, Q321I, Q321L, Q321F, Q321M. For instance, a modified enzyme can include one of these mutations at each of these sites (SEQ ID NO: 16).

In one embodiment, a modified enzyme can include single-site mutations at one or more of positions 13, 18, 19, 31, 34, 49, 83, 103, 119, 141, 184, or 321, as compared to SEQ ID NO: 5 in which each single-site mutation has a ΔΔG value of about 2.0 kcal/mol or greater. For instance, a modified enzyme can include one or more of the following single-site mutations: one of A13Y, A13W, A13I, A13F; one of A18L, A18F, A18I, A18W; one of S19Y, S19W; S31L; A34L; A49G; one of R83L, R83F, R83I, R83V; A103I; one of G119L, G119F; Q141I; G184W; one of Q321T, Q321V, Q321I, Q321L. For instance, a modified enzyme can include one of these mutations at each of these sites (SEQ ID NO: 17).

A transformed cell or a cell-free expression system that can express a polypeptide as described is also encompassed herein. In one embodiment, a transformed cell can be derived from a halophile that naturally expresses a halophilic and thermophilic wild-type enzyme as described, e.g., a halophile that naturally produces the wild-type enzyme on which a modified enzyme is based. In other embodiments, a transformed cell can be of a different type than the wild-type cell that naturally expresses a thermophilic and halophilic enzyme and can be transformed to express either a wild-type or a modified halophilic and thermophilic enzymatic polypeptide.

An enzyme can be expressed by transformation of a suitable host organism, for example, by use of either prokaryotic or eukaryotic host cells. Examples of host cell types include, without limitation, bacterial cells (e.g., *E. coli*), yeast cells (e.g., *pichia, S. cerevisiae*), cultured insect cell lines (e.g., *Drosophila*), plant cell lines (e.g., maize, tobacco, rice, sugarcane, potato tuber), mammalian cells lines (e.g., Chinese Hamster Ovary (CHO)). In one embodiment, a recombinant host cell system can be selected that processes and post-translationally modifies nascent polypeptides in a manner desired to produce the final catalytic polypeptide.

A nucleic acid sequence that encodes an enzyme may be placed in an expression vector for expression in the selected host. Such expression vectors can generally comprise a transcriptional initiation region linked to the nucleic acid sequence that encodes the enzyme. An expression vector can also include a plurality of restriction sites for insertion of the nucleic acid to be under the transcriptional regulation of various control elements. The expression vector additionally may contain selectable marker genes. Suitable control elements such as enhancers/promoters, splice junctions, polyadenylation signals, etc. may be placed in close proximity to the coding region to permit proper initiation of transcription and/or correct processing of the primary transcript, i.e., the coding region for the enzyme. Alternatively, the coding region utilized in an expression vector may contain endogenous enhancers/promoters, splice junctions, intervening sequences, polyadenylation signals, etc., or a combination of both endogenous and exogenous control elements.

An expression vector generally includes in the 5'-3' direction of transcription, a promoter, a transcriptional and translational initiation region, a DNA sequence that encodes the enzyme, and a transcriptional and translational termination region functional in the host cell. In one embodiment, a T7-based vector can be used, which can include at least the following components: an origin of replication, a selectable antibiotic resistance gene (e.g., ampr, tetr, chlrr), a multiple cloning site, T7 initiator and terminator sequences, a ribosomal binding site, and a T7 promoter.

In general, any suitable promoter may be used that is capable of operative linkage to the heterologous DNA such that transcription of the DNA may be initiated from the promoter by an RNA polymerase that may specifically recognize, bind to, and transcribe the DNA in an open reading frame. Some useful promoters include constitutive promoters, inducible promoters, regulated promoters, cell specific promoters, viral promoters, and synthetic promoters. Moreover, while promoters may include sequences to which an RNA polymerase binds, this is not a requirement. A promoter may be obtained from a variety of different sources. For example, a promoter may be derived entirely from a native gene of the host cell, be composed of different elements derived from different promoters found in nature, or be composed of nucleic acid sequences that are entirely synthetic. A promoter may be derived from many different types of organisms and tailored for use within a given cell. For example, a promoter may include regions to which other regulatory proteins may bind in addition to regions involved in the control of the protein translation, including coding sequences.

A translation initiation sequence can be derived from any source, e.g., any expressed *E. coli* gene. Generally, the gene is a highly-expressed gene. A translation initiation sequence can be obtained via standard recombinant methods, synthetic techniques, purification techniques, or combinations thereof, which are all well known. Alternatively, translational start sequences can be obtained from numerous commercial vendors. (Operon Technologies; Life Technologies Inc.).

The termination region may be native with the transcriptional initiation region, may be native with the coding region, or may be derived from another source. Transcription termination sequences recognized by the transformed cell are regulatory regions located 3' to the translation stop codon, and thus together with the promoter flank the coding sequence. Examples include transcription termination sequences derived from genes with strong promoters, such as the trp gene in *E. coli*, as well as other biosynthetic genes.

Vectors that may be used include, but are not limited to, those able to be replicated in prokaryotes and eukaryotes. For example, vectors may be used that are replicated in bacteria, yeast, insect cells, and mammalian cells. Examples of vectors include plasmids, phagemids, bacteriophages, bacterial artificial chromosomes, viruses (e.g., baculovirus), cosmids, F-factors, and bacterial artificial chromosomes. Specific vectors may be used for specific cells types. Additionally, shuttle vectors may be used for cloning and replication in more than one cell type. Such shuttle vectors are known in the art. The vector may, if desired, be a bifunctional expression vector that may function in multiple hosts.

An expression vector that encodes a PHADase may be introduced into a host cell by any method known to one of skill in the art and the nucleic acid constructs may be carried extrachromosomally within a host cell or may be integrated into a host cell chromosome, as desired. A vector for use in a prokaryote host, such as a bacterial cell, includes a replication system allowing it to be maintained in the host for expression or for cloning and amplification. A vector may be present in the cell in either high- or low-copy number. Generally, about 5 to about 200, and usually about 10 to about 150 copies, of a high-copy number vector are present within a host cell. A host cell containing a high-copy number vector will preferably contain at least about 10, and more preferably, at least about 20 plasmid vectors. Generally, about 1 to 10, and usually about 1 to 4 copies, of a low-copy number vector will be present in a host cell.

In many embodiments, bacteria are used as host cells. Examples of bacteria include, but are not limited to, Gram-negative and Gram-positive organisms. In one embodiment an *E. coli* expression system suitable for T7 protein expression may be used. Examples of T7 expression strains can include, without limitation, BL21(DE3), BL21(DE3)pLysS, BLR(DE3)pLysS, Tuner™(DE3)pLysS, Tuner™(DE3), Lemo21(DE3), NiCO2(DE3), Origami™2(DE3), Origami™ B(DE3), SHuffle® T7 Express, HMS174(DE3), HMS174(DE3)pLysS, DH5alphaE, Rosetta™2(DE3), Rosetta™2(DE3)pLysS, NovaBlue(DE3), Rosetta-gami™ B, Rosetta-gami™ B(DE3), Rosetta-gami™ B(DE3)pLysS, RosettaBlue™ (DE3), Novagen(DE3), Novagen(DE3) pLysS.

An expression vector may be introduced into bacterial cells by commonly used transformation/infection procedures. A nucleic acid construct containing an expression cassette can be integrated into the genome of a bacterial host cell through use of an integrating vector. Integrating vectors usually contain at least one sequence that is homologous to the bacterial chromosome that allows the vector to integrate. Integrating vectors may also contain bacteriophage or transposon sequences. Extrachromosomal and integrating vectors may contain selectable markers to allow for the selection of bacterial strains that have been transformed.

Useful vectors for an *E. coli* expression system may contain constitutive or inducible promoters to direct expression of either fusion or non-fusion proteins. With fusion vectors, a number of amino acids are usually added to the expressed target gene sequence. Additionally, a proteolytic cleavage site may be introduced at a site between the target recombinant protein and the fusion sequence. Once the fusion protein has been purified, the cleavage site allows the target recombinant protein to be separated from the fusion sequence. Enzymes suitable for use in cleaving the proteolytic cleavage site include TEV, Factor Xa and thrombin. Fusion expression vectors which may be useful in the present can include those which express, for example and without limitation, Maltose Binding Protein (MBP), Thioredoxin (THX), Chitin Binding Domain (CBD), Hexahistadine tag (His-tag) (SEQ ID NO: 18), glutathione-S-transferase protein (GST), FLAG peptide, N-utilization substance (NusA), or Small ubiquitin modified (SUMO) fused to the target recombinant enzyme.

Methods for introducing exogenous DNA into a host cell are available in the art and can include the transformation of bacteria treated with $CaCl_2$) or other agents, such as divalent cations and DMSO. DNA can also be introduced into host cells by electroporation, use of a bacteriophage, ballistic transformation, calcium phosphate co-precipitation, spheroplast fusion, electroporation, treatment of the host cells with lithium acetate, or by electroporation. Transformation procedures usually vary with the bacterial species to be transformed.

Following transformation or transfection of a nucleic acid into a cell, the cell may be selected for the presence of the nucleic acid through use of a selectable marker. A selectable marker is generally encoded on the nucleic acid being introduced into the recipient cell. However, co-transfection of selectable marker can also be used during introduction of nucleic acid into a host cell. Selectable markers that can be expressed in the recipient host cell may include, but are not limited to, genes that render the recipient host cell resistant to drugs such as actinomycin CI, actinomycin D, amphotericin, ampicillin, bleomycin, carbenicillin, chloramphenicol, geneticin, gentamycin, hygromycin B, kanamycin monosulfate, methotrexate, mitomycin C, neomycin B sulfate, novobiocin sodium salt, penicillin G sodium salt, puromycin dihydrochloride, rifampicin, streptomycin sulfate, tetracycline hydrochloride, and erythromycin. Selectable markers may also include biosynthetic genes, such as those in the histidine, tryptophan, and leucine biosynthetic pathways. Upon transfection or transformation of a host cell, the cell is placed into contact with an appropriate selection agent.

To encourage simultaneous decontamination and degradation of a biopolymer, and referring again to FIG. 1, a polypeptide including an enzyme as described, and/or a cell that expresses the enzyme can be located in a reaction chamber 12 of a bioreactor 10. For instance, in one embodiment, a reaction chamber 12 can include a bed 13 that can include a polymer to be processed and enzyme and/or enzyme producing cells adsorbed onto or otherwise contained within the bed. An enzyme and/or enzyme expressing cell can be pre-loaded onto a bed 13, can be periodically or continuously fed to the reactor 10, e.g., via an inlet 14, or some combination thereof.

A second inlet 16 can provide continuous or periodic feed of a polymer to a reaction chamber 12 for simultaneous degradation and decontamination in the reaction zone 12.

Any PHA polymer can be degraded and decontaminated according to the present disclosure. A PHA can be a homopolymer or a copolymer. In one embodiment, a PHB-containing material can be fed to the reaction zone 12.

Examples of monomer units that can be incorporated in PHA for processing as described can include 2-hydroxybutyrate, glycolic acid, 3-hydroxybutyrate, 3-hydroxypropionate, 3-hydroxyvalerate, 3-hydroxyhexanoate, 3-hydroxyheptanoate, 3-hydroxyoctanoate, 3-hydroxynonanoate, 3-hydroxydecanoate, 3-hydroxydodecanoate, 4-hydroxybutyrate, 4-hydroxyvalerate, 5-hydroxyvalerate, and 6-hydroxyhexanoate. Examples of PHA homopolymers include poly 3-hydroxyalkanoates (e.g., poly 3-hydroxypropionate (PHP), poly 3-hydroxybutyrate (PHB), poly 3-hydroxyvalerate (PHV), poly 3-hydroxyhexonoate (PHH), poly 3-hydroxyoctanoate (PHO), poly 3-hydroxydecanoate (PHD), and poly 3-hydroxy-5-phenylvalerate (PHPV)), poly 4-hydroxyalkanoates (e.g., poly 4-hydroxybutyrate (hereinafter referred to as PHB), and poly 4-hydroxyvalerate (hereinafter referred to as PHV)), or poly 5-hydroxyalkanoates (e.g., poly 5-hydroxyvalerate (hereinafter referred to as PHV)).

In certain embodiments, the PHA can be a copolymer (containing two or more different monomer units) in which the different monomers are randomly distributed in the polymer chain. Examples of PHA copolymers include poly 3-hydroxybutyrate-co-3-hydroxypropionate (hereinafter referred to as PHB3HP), poly 3-hydroxybutyrate-co-4-hydroxybutyrate (hereinafter referred to as P3HB4HB), poly 3-hydroxybutyrate-co-4-hydroxyvalerate (hereinafter referred to as PHB4HV), poly 3-hydroxybutyrate-co-3-hydroxyvalerate (hereinafter referred to as PHB3HV), poly 3-hydroxybutyrate-co-3-hydroxyhexanoate (hereinafter referred to as PHB3HH) and poly 3-hydroxybutyrate-co-5-hydroxyvalerate (hereinafter referred to as PHB5HV).

In one embodiment, the polymer fed to the reactor 10 via inlet 16 can be preprocessed, for instance, chopped, ground, etc., to provide a large surface area for interaction with enzyme within the reaction zone. Inlet 16 can feed particulate matter, including post-consumer PHA, through the inlet 16, e.g., a screw type feeder, which can be positioned at the side of the reactor generally near the top of the reaction zone 12, e.g., above the bed 13.

In one embodiment, a polymer feed such as inlet 16 and/or inlet 14 can also be utilized for introduction of a suitable salt to the reaction bed, e.g., an alkali metal or alkaline earth metal salt such as, without limitation, sodium chloride, potassium chloride, calcium chloride, magnesium chloride, sodium bromide, potassium bromide, sodium iodide, potassium iodide, or mixtures thereof, to maintain a desired salt content in the reaction bed. Introduction of a salt to the reaction bed 12 can be carried out continuously or periodically, as desired, during the course of a depolymerization reaction.

In one embodiment, an inlet 14 can provide flow through the bed 13 to encourage the enzyme to react with the biopolymer. In some embodiments, inlet 14 can provide a flow upward through the reaction chamber 12 and inlet 16 can provide continuous or periodic flow of polymer into the reaction zone 12. The flow fed to the reactor 10 via inlet 14 can be buffered as desired to provide the optimal pH for the degradation reaction. For instance, an aqueous flow at a pH of from about 7 to about 9, or from about 7 to about 8 in some embodiments, can be fed via inlet 14, optionally in conjunction with periodic or continuous inclusion of enzyme.

In one embodiment, inlet 14 can be near the bottom of a reactor 10 and can provide a continuous flow upward through the reactor during the reaction period. As the flow from inlet 14 moves upward through the reactor 10, enzyme and salt can likewise move upward through the bed 13, and after degrading PHA in the lower regions of the bed, can contact non-degraded polymer at the upper end of the bed 13. As such, it may be beneficial in some embodiments to provide salt to the reaction zone 12 via the upward flow from inlet 14. During the ongoing degradation process, volume of polymer initially fed to the bed 13 can degrade and additional polymer can be added to the reactor at the top of the bed 13. Thus, enzyme can contact the newly fed polymer, and the rate of addition of polymer can be roughly equal to the rate of enzymatic hydrolysis.

The bioreactor 10 can also include an outlet 18 above the bed 13 through which the degraded and decontaminated polymer can exit the reactor 10. Flow through the reactor can be controlled such that the retention time within the bed provides contact between the enzyme and the polymer suitable for hydrolysis reaction. The top of the bed 13 can be fitted in one embodiment with a plate to prevent remaining polymer particles to exit via outlet 18.

Following exit via outlet 18, the reaction product flow can pass through a separator 20, within which any escaped polymer particulate and/or enzyme can be separated from the reactor outflow. For instance, in one embodiment, enzyme can be retained in the reaction zone 12 by immobilization on a support such as a polymeric bead, gel, etc. and the separator 20 can include a physical separation operation to remove any such support material from the outflow and return it to the reactor via line 22.

A system can optionally include a separation operation 15 that can separate the product stream from the reactor into various products, e.g., PHA degradation products (re-usable monomers and/or oligomers) 17, decontaminated waste 19, other polymers 21, etc., for instance via a distillation separation or the like.

The present disclosure may be better understood with reference to the Examples set forth below.

Example 1

The PHBDase sequence from *Halomonas aquamarina* (Taxonomy: Bacteria; Proteobacteria; Gammaproteobacteria; Oceanospirillales; Halomonadaceae; *Halomonas*) was utilized as a representative of an enzyme from a halophilic organism. The sequence SEQ ID NO: 1 (GenBank Accession No. WP_089674669.1) consists of a 355-amino acid protein including a 24-amino acid N-terminal signal sequence (underlined). Active site consensus structures are shown in bold, and include a 9-amino acid fragment (SEQ ID NO: 2) beginning at A71, a 10-amino acid fragment (SEQ ID NO: 3) beginning at R125, and a 7-amino acid fragment (SEQ ID NO: 4) beginning at G254.

Since the signal sequence is proteolyzed as part of the export process, all work in this example utilized the 332-amino acid protein (SEQ ID NO: 5), which begins at with a methionine followed by the glutamic acid at position 25 of SEQ ID NO: 1.

The mature 332-amino acid primary sequence (SEQ ID NO: 5) had a molecular weight of 35.7 kDa and a 4.37 isoelectric point (pI). This pI is comprised by 12.95% negatively charged and 5.1% positively charged amino acid residues. There are 8 cysteine residues in the protein.

The mature 332-amino acid primary sequence (SEQ ID NO: 5) was converted into a three-dimensional model by the technique of molecular threading. Briefly, the sequence was "threaded" in three-dimensional space along the backbone of a structure from a homologous enzyme. Once the backbone atoms were fixed in space, the model sidechain atoms were used as a guide (to the CB atom) and a model of the sequence amino acids was built onto the mainchain model. The premiere code for this calculation was LOMETS2 (Zheng and Zhang, 2019). To determine the best fit, the *H. aquamarina* sequence was threaded against three homologue PHBDase proteins produced by *Paucimonas lemoignei* (2VTV), *Bordetella parapertussis* (3D0K), and *Penicillium funiculosum* (2D80). Model 'correctness' was gauged by both the RMSD (mainchain to Cβ atoms) as well as a proprietary scoring function. By both measures, the best model for the *L. thermophila* enzyme was the 2D80 *P. funiculosum* structure.

Figure 2:
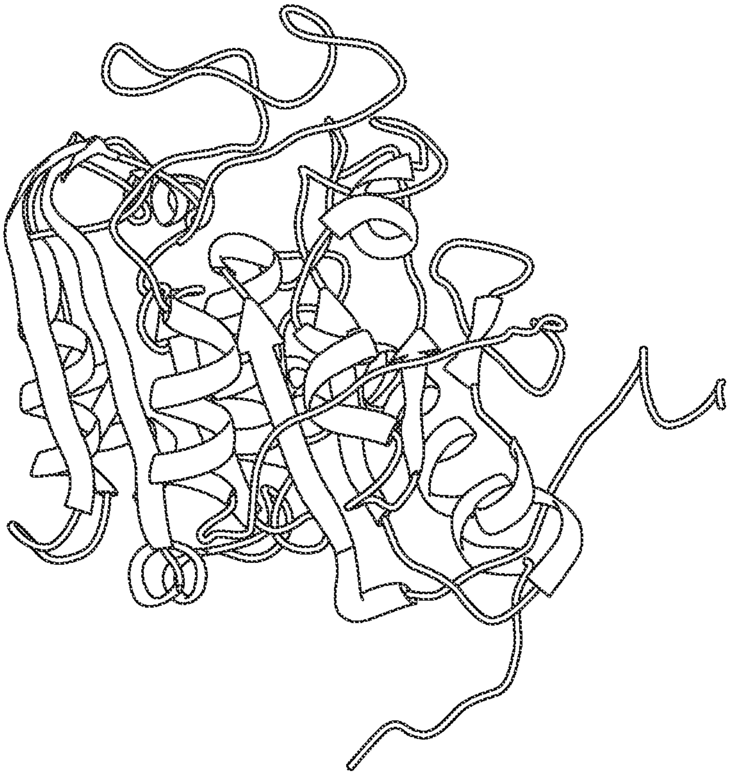
FIG. 2 illustrates an energy minimized *H. aquamarina* PHBDase model.

The model produced by the threading algorithm was not energy-minimized and there was some expected degree of unfavored sidechain torsional angles. To correct these, the *H. aquamarina* model was placed into a 40 Å×40 Å×40 Å explicit water box (using the program VMD, Humphrey et al., 1996) and subjected to 5 ns of molecular dynamics (MD). This was accomplished in a three-step protocol. In the first step, all protein atoms were fixed and the solvent was minimized with 1 ns of NPT MD using the NAMD molecular dynamics package (Phillips et al., 2005). The final structure from the first round was subjected to 2 ns of NVT MD with only the sidechain atoms fixed. This round allowed the protein backbone to minimize. The final structure from that round was subjected to 2 ns of NVT MD without any atom position restraints. The final structure represented the energy minimized *H. aquamarina* model (FIG. 2). All sidechains were within allowed Ramachandran space.

The model was used for all subsequent studies after all solvent was removed from the coordinate file. As shown in FIG. 2, the structure includes the central β-sheet structure that is composed of six central parallel strands flanked on one side by an antiparallel strand. There are 9 α-helical regions (3 of which are short 2-3 turn helices). Five of the helices directly flank the central β-sheet. The model has a RMSD of 2.4 Å on mainchain atoms with the 2D80 structure and a LOMETS score of −4.1, which indicates a robust threading result.

Example 2

All chemicals were purchased from Sigma-Aldrich, including all buffers, media, isopropyl-β-D-thiogalactoside, antibiotics, and polyhydroxybutyrate granules. Chromatography resins were also from Sigma-Aldrich. All laboratory supplies were purchased from Fisher Scientific. Competent *E. coli* were purchased from New England Biolabs, Inc.

The amino acid sequence of the *H. aquamarina* PHBDase (SEQ ID NO: 1) was utilized to construct a recombinant DNA expression system. The first 24 amino acids of the sequence corresponding to the putative signal sequence were removed from the protein and replaced by the thioredoxin (THX) protein (SEQ ID NO: 14; aa 2-109 UniProtKB Accession No. sp[P0AA25]) to drive solubility and folding. This THX sequence was followed by a short (GS)3 linker (SEQ ID NO: 19) followed by the sequence: MHHHHHHGSENLYFQS (SEQ ID NO: 6). SEQ ID NO: 6 provides a 6-histidine nickel chelating sequence followed by the TEV protease cleavage site. Upon cleavage the recombinant protein had an N-ter sequence that began SMEEE . . . (SEQ ID NO: 7), i.e., a serine followed by SEQ ID NO: 5. The resulting sequence was reverse translated to DNA and codon optimized for expression in *E. coli* using the program Gene Designer from ATUM, Inc. The gene was assembled using standard PCR techniques by ATUM, Inc. and cloned into the expression vector p454-MR (ampr, medium strength ribosomal binding site) (ATUM, Inc.). The insert was verified by DNA sequencing after construction.

The expression plasmid was used to transform chemically competent Origami™ 2-(DE3) bacteria. Single colonies were selected from LB-Amp plates and used for expression screening. Colonies were grown at 30° C. for 12 hours in LB media supplemented with 100 μg/mL ampicillin. This culture was used to inoculate fresh LB-AMP flasks at a 1:100 inoculum. These cultures were grown at 30° C. until OD595=0.4 (typically 4 hours) at which time IPTG was added to a final concentration of 1 mM. Growth was continued for 12 hours. Cells were harvested by centrifugation at 10,000×g for 15 minutes and frozen at −80° C. until use (minimal time frozen was 24 hours). Cells were thawed on ice and were resuspended in Buffer A (0.5 M NaCl, 20 mM Tris-HCl, 5 mM imidazole, pH 7.9) (typically 1 mL per gram of cells). Cells were disrupted via two passes through a French Press followed by centrifugation at 30,000×g for 30 minutes. The crude extract was mixed with an equal volume of charged His-Bind resin slurry and the mixture was poured into 5 cm×4.9 cc column. The column was washed with 10 column volumes of wash buffer (0.5 M NaCl, 20 mM Tris-HCl, 60 mM imidazole, pH 7.9) at a flow rate of 0.2 mL/min. Enzyme was eluted from the column with the addition of 3 column volumes of 0.5 M NaCl, 20 mM Tris-HCl, 1.0 M imidazole, pH 7.9. Fractions were collected (1.0 mL). Fractions containing enzyme were pooled after analysis by SDS PAGE. The pooled fractions were applied to a 70 cm×4.9 cc Sephadex® G-75 column (10 mM Tris-HCl, pH 7.5, 1 mM EDTA). Fractions containing homogeneous protein were pooled (after inspection by SDS PAGE), concentrated to 5 mg/ml via Centricon® filters. Enzyme was stored frozen at −20° ° C. until use. The TRX-histidine tag region was removed from the enzymes using TEV protease. Protein was diluted to 1.0 mg/ml into 10 mM Tris-HCl, pH 7.5, 25 mM NaCl. 100 U of TEV protease was added per mg of enzyme (approximate ratio of 1:100 (w/w). The reaction was allowed to proceed for 16 hours at 4° C. The mixture was passed over a charged nickel column. One column volume of eluent was collected representing purified tag-free enzyme.

A turbidometric assay was employed to measure PHBDase activity under various conditions. The standard reaction (final volume=1.0 mL) contained 200 mg/L of PHB granules (that were previously stably suspended via sonication), 1 mM $CaCl_2$), 10 mM KCl, 0.5 M NaCl, 20 mM buffer at various pH values. The reaction was initiated after the addition of enzyme and monitored at 650 nm in Applied Photophysics spectrapolarometer in absorbance mode. The reaction was gently stirred and maintained at a constant temperature. OD measurements (typically starting in the range of 2-3) were converted to percent OD remaining as a function of time. All kinetic parameters are calculated per Segel (1993).

Figure 3:
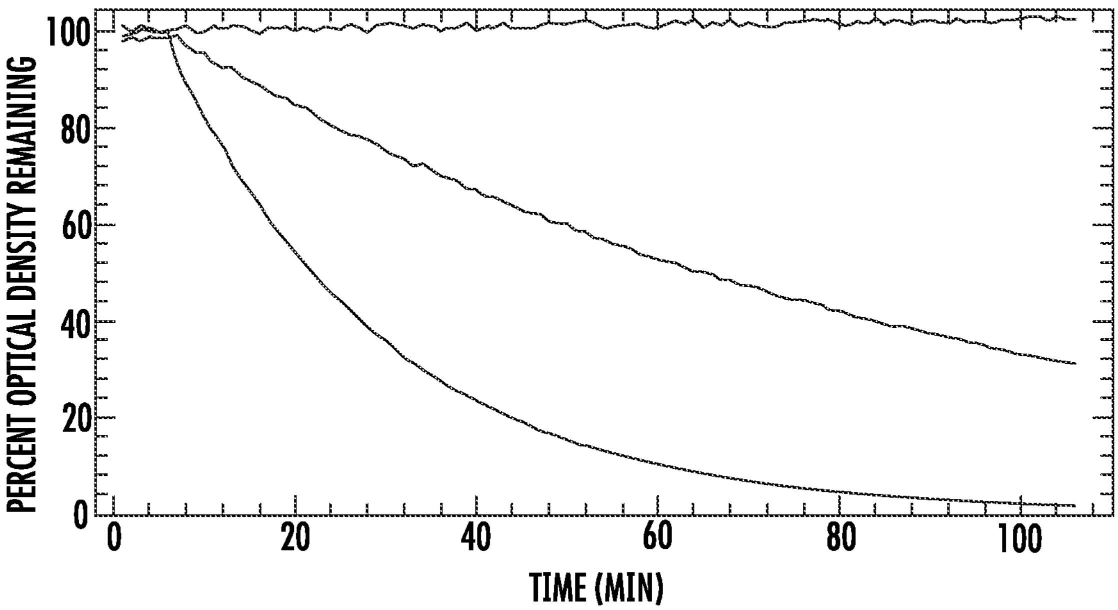
FIG. 3 graphically compares the degradation of PHB granules by action of the purified wild-type *H. aquamarina* PHBDase at two different enzyme concentrations with a no-enzyme control reaction.

The purified *H. aquamarina* PHBDase reaction is shown in FIG. 3. The degradation reaction is shown below.

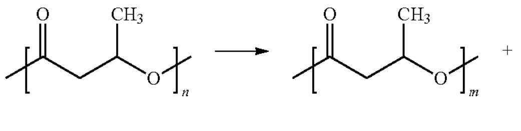

-continued

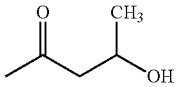

in which m<<n and represents small oligomers, typically 2-4 mers.

The enzyme was fully capable of degrading PHB granules (as measured by the turbidometric assay). Kinetic constants were calculated from the assays and are shown in Table 2, below, in which $K_m$ is the Michaelis constant, $k_{cat}$ is the catalytic rate constant, $k_{cat}K_m^{-1}$ is the specificity, $pH_{opt}$ is the optimal pH of reaction, and $T_{opt}$ is the optimal temperature of reaction. The values in the table are the mean of three independent determinations and values in parenthesis are the standard deviation.

TABLE 2

| $K_m$ (µM) | $k_{cat}$ ($s^{-1}$) | $k_{cat}K_m^{-1}$ ($s^{-1}µM^{-1}$) | $pH_{opt}$ | $T_{opt}$ (° C.) |
|---|---|---|---|---|
| 14.7 (0.4) | 4.2 (0.2) | 0.29 | 6.4 | 40.1 (0.3) |

Example 3

A combination of approaches was utilized to identify stabilizing mutants of the *H. aquamarina* PHBDase described above.

Cavities were identified either by direct observation or using the programs CAVER (Jurcik et al., 2018) or Beta-CavityWeb (Kim et al., 2015). Once a cavity was identified, an amino acid in the cavity was selected for mutation. Selection criteria was based on:

1) the sidechain of the residue pointed into the cavity;
2) the mutation increased cavity packing (using the predominant torsion angle for that amino acid); and
3) the mutation could be accommodated in the cavity by neighboring residue sidechains (meaning all steric, electrostatic, or hydrogen bonding was satisfied).

Amino acids were modeled into the cavity using the SWAPAA algorithm in the Chimera package. This analysis identified 11 cavities that were not optimally/maximally packed. The ΔΔG values were derived as $\Delta G_{wt}$-$\Delta G_{mut}$ and show the stabilizing energetics of the single amino acid substitution. Any potential mutations that are within active site consensus structures (SEQ ID NO: 2-4) were excluded from use.

In addition, the *H. aquamarina* model was used to create a population of structure files, each with a single amino acid substitution. All 19 amino acids were substituted into each position for a total of 6308 structures (332 aa enzyme×19 amino acids). Each structure was energy minimized in implicit solvent via 2 ns of NVT molecular dynamics. The calculations were run on the XSEDE national computing resource BRIDGES utilizing 10 GPUs and 124 hours computation time. Using the standard free energy calculation techniques for molecular dynamics trajectories (Zhang et al., 2012; Aldeghi et al., 2019), a ΔG value was calculated for each protein mutant.

Figure 4:
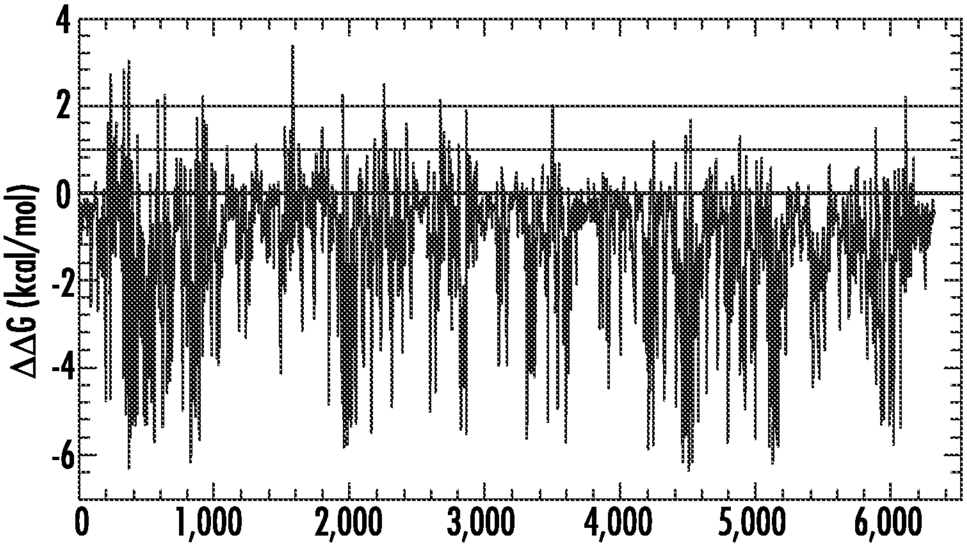
FIG. 4 graphically illustrates Gibbs free energy differences for individual amino acids of a PHBDase upon substitution of different amino acids into each position of a wild-type PHBDase.

A python script was used to extract the ΔG values from the output files and to calculate the ΔΔG values. The results are shown in FIG. 4. As expected, most single-point mutations were found to be destabilizing (values below the ΔΔG=0 line). A much smaller fraction resulted in a more stable protein (values above the ΔΔG=0 line). FIG. 4 is arrayed with the first 19 positions corresponding to all the possible single-point mutants at position one of the protein, the next 19 corresponding to position two mutants, etc.

Upon all the mutational analyses (cavity filling, surface charge alteration, and straight free energy calculations), there were 11 cavity/void mutations, 4 surface charge mutations, and 9 additional mutations identified in the straight free energy calculation that can be made to drive thermal/thermodynamic stability and solubility.

Tables 3-14 present the results for these 24 positions on SEQ ID NO: 5 that were found to have potential single-site mutations that resulted in a positive ΔΔG value. These tables show the ΔΔG value for each possible amino acid substitution into each of these 20 positions.

TABLE 3

| Position 12 - WT - G | | Position 13 - WT - A | |
|---|---|---|---|
| Mutant | ΔΔG (kcal/mol) | Mutant | ΔΔG (kcal/mol) |
| P | 1.650 | Y | 2.721 |
| L | 1.603 | W | 2.455 |
| F | 1.135 | I | 2.321 |
| W | 1.081 | F | 2.177 |
| N | 1.019 | L | 1.697 |
| I | 0.839 | V | 1.455 |
| H | 0.457 | C | 0.532 |
| Y | 0.382 | M | 0.374 |
| V | 0.382 | T | −0.919 |
| K | 0.276 | H | −1.939 |
| C | 0.217 | S | −2.145 |
| Q | 0.213 | G | −2.290 |
| M | 0.191 | K | −2.347 |
| R | 0.142 | P | −3.045 |
| E | −0.049 | R | −3.444 |
| T | −0.143 | N | −4.259 |
| A | −0.347 | E | −4.370 |
| S | −0.391 | Q | −4.444 |
| D | −0.655 | D | −4.713 |

TABLE 4

| Position 15 - WT - N | | Position 18 - WT - A | |
|---|---|---|---|
| Mutant | ΔΔG (kcal/mol) | Mutant | ΔΔG (kcal/mol) |
| F | 1.660 | L | 2.848 |
| L | 1.254 | F | 2.495 |
| V | 1.138 | I | 2.437 |
| P | 0.963 | W | 2.430 |
| W | 0.801 | V | 1.861 |
| K | 0.699 | M | 1.801 |
| I | 0.657 | Y | 1.710 |
| M | 0.535 | C | 1.121 |
| T | 0.153 | T | 1.041 |
| A | −0.038 | S | −0.186 |
| C | −0.056 | H | −0.305 |
| Y | −0.134 | N | −0.415 |
| R | −0.140 | G | −1.798 |
| Q | −0.166 | R | −2.111 |
| E | −0.172 | K | −2.291 |
| S | −0.394 | P | −2.435 |
| H | −0.467 | Q | −3.217 |
| D | −0.946 | E | −3.707 |
| G | −1.431 | D | −4.191 |

TABLE 5

| Position 19 - WT - S | | Position 31 - WT - S | |
|---|---|---|---|
| Mutant | ΔΔG (kcal/mol) | Mutant | ΔΔG (kcal/mol) |
| Y | 3.031 | L | 2.145 |
| W | 2.218 | I | 1.852 |
| F | 0.857 | W | 1.706 |
| I | −0.077 | F | 1.336 |
| V | −0.126 | V | 1.248 |
| L | −0.190 | M | 1.218 |
| C | −0.467 | Y | 1.014 |
| T | −0.774 | T | 0.509 |
| M | −0.781 | A | 0.450 |
| A | −1.524 | C | 0.295 |
| K | −3.182 | H | −0.538 |
| G | −3.481 | N | −1.014 |
| H | −3.529 | Q | −1.214 |
| E | −3.654 | P | −1.380 |
| N | −3.959 | K | −1.446 |
| R | −4.075 | R | −1.481 |
| P | −4.616 | G | −1.590 |
| D | −4.990 | E | −1.979 |
| Q | −5.056 | D | −2.053 |

TABLE 6

| Position 34 - WT - A | | Position 46 - WT - M | |
|---|---|---|---|
| Mutant | ΔΔG (kcal/mol) | Mutant | ΔΔG (kcal/mol) |
| L | 2.254 | W | 1.720 |
| F | 1.839 | C | 0.795 |
| I | 1.724 | L | 0.677 |
| W | 1.619 | F | 0.528 |
| M | 1.089 | I | 0.418 |
| H | 1.017 | Y | 0.114 |
| C | 0.767 | V | −0.442 |
| V | 0.715 | A | −1.389 |
| Y | 0.659 | T | −1.827 |
| G | 0.305 | S | −2.528 |
| S | 0 | G | −3.475 |
| T | −0.090 | H | −3.662 |
| E | −0.603 | P | −3.904 |
| Q | −0.769 | N | −4.237 |
| P | −1.675 | K | −4.388 |
| N | −1.767 | R | −4.493 |
| K | −2.058 | E | −4.551 |
| D | −2.323 | Q | −4.700 |
| R | −2.390 | D | −5.118 |

TABLE 7

| Position 49 - WT - A | | Position 50 - WT - G | |
|---|---|---|---|
| Mutant | ΔΔG (kcal/mol) | Mutant | ΔΔG (kcal/mol) |
| G | 2.230 | L | 1.583 |
| L | 1.671 | F | 1.096 |
| F | 1.560 | W | 1.064 |
| W | 1.352 | I | 0.697 |
| V | 0.995 | V | 0.518 |
| I | 0.795 | T | 0.476 |
| C | 0.777 | H | 0.248 |
| Y | 0.408 | Y | 0.093 |
| M | 0.215 | C | −0.125 |
| T | 0.178 | M | −0.367 |
| S | −0.554 | K | −0.799 |
| N | −1.508 | S | −0.847 |
| R | −1.594 | A | −1.063 |
| P | −1.772 | Q | −1.150 |

TABLE 7-continued

| Position 49 - WT - A | | Position 50 - WT - G | |
|---|---|---|---|
| Mutant | ΔΔG (kcal/mol) | Mutant | ΔΔG (kcal/mol) |
| H | −1.929 | R | −1.156 |
| K | −2.017 | E | −1.260 |
| E | −2.433 | N | −1.286 |
| Q | −3.460 | P | −2.203 |
| D | −3.705 | D | −2.497 |

TABLE 8

| Position 58 - WT - A | | Position 80 - WT - E | |
|---|---|---|---|
| Mutant | ΔΔG (kcal/mol) | Mutant | ΔΔG (kcal/mol) |
| L | 1.099 | L | 1.499 |
| W | 0.696 | W | 1.220 |
| F | 0.673 | V | 1.082 |
| N | 0.640 | M | 1.050 |
| Y | 0.624 | T | 0.910 |
| E | 0.551 | F | 0.852 |
| I | 0.533 | I | 0.642 |
| Q | 0.506 | S | −0.029 |
| H | 0.433 | A | −0.254 |
| K | 0.414 | K | −0.467 |
| S | 0.334 | N | −0.555 |
| V | 0.281 | H | −0.557 |
| M | 0.272 | Q | −0.680 |
| T | 0.255 | C | −0.729 |
| C | 0.232 | R | −1.024 |
| R | 0.160 | Y | −1.135 |
| P | 0.073 | D | −1.460 |
| G | −0.097 | P | −2.211 |
| D | −0.217 | G | −2.317 |

TABLE 9

| Position 83 - WT - R | | Position 89 - WT - L | |
|---|---|---|---|
| Mutant | ΔΔG (kcal/mol) | Mutant | ΔΔG (kcal/mol) |
| L | 3.399 | K | 0.176 |
| F | 2.899 | N | 0.098 |
| I | 2.531 | H | 0.070 |
| V | 2.033 | W | 0.062 |
| T | 1.617 | F | 0.040 |
| M | 1.570 | R | 0.017 |
| A | 1.459 | Q | −0.028 |
| W | 1.435 | E | −0.043 |
| Y | 0.413 | M | −0.063 |
| S | 0.353 | I | −0.096 |
| C | 0.141 | C | −0.099 |
| E | 0.003 | V | −0.122 |
| H | −0.158 | Y | −0.142 |
| K | −0.189 | A | −0.204 |
| N | −0.235 | S | −0.264 |
| Q | −0.345 | D | −0.329 |
| D | −1.064 | T | −0.349 |
| P | −1.562 | G | −0.571 |
| G | −1.709 | P | −0.827 |

TABLE 10

| Position 95 - WT - Q | | Position 103 - WT - A | |
|---|---|---|---|
| Mutant | ΔΔG (kcal/mol) | Mutant | ΔΔG (kcal/mol) |
| L | 1.507 | I | 2.263 |
| I | 1.097 | Y | 1.979 |
| W | 1.021 | L | 1.907 |
| V | 0.878 | F | 1.872 |
| F | 0.828 | W | 1.840 |

TABLE 10-continued

| Position 95 - WT - Q | | Position 103 - WT - A | |
|---|---|---|---|
| Mutant | ΔΔG (kcal/mol) | Mutant | ΔΔG (kcal/mol) |
| M | 0.474 | V | 1.804 |
| T | 0.448 | M | 1.326 |
| E | 0.034 | C | 0.938 |
| A | −0.042 | T | −0.264 |
| S | −0.137 | S | −1.132 |
| H | −0.167 | K | −2.031 |
| C | −0.171 | R | −2.169 |
| K | −0.185 | H | −2.502 |
| N | −0.188 | G | −2.652 |
| Y | −0.218 | P | −3.081 |
| D | −0.517 | Q | −3.737 |
| R | −0.520 | N | −3.795 |
| P | −0.674 | E | −4.510 |
| G | −1.353 | D | −4.818 |

TABLE 11

| Position 119 - WT - G | | Position 141 - WT - Q | |
|---|---|---|---|
| Mutant | ΔΔG (kcal/mol) | Mutant | ΔΔG (kcal/mol) |
| L | 2.482 | I | 2.125 |
| F | 2.063 | Y | 1.705 |
| W | 1.855 | W | 1.564 |
| I | 1.726 | L | 1.483 |
| M | 1.639 | V | 1.288 |
| Y | 1.601 | F | 1.145 |
| T | 1.507 | M | 0.844 |
| V | 1.400 | T | 0.673 |
| C | 1.242 | C | 0.405 |
| H | 0.883 | H | 0.322 |
| S | 0.657 | S | 0.319 |
| N | 0.611 | K | 0.088 |
| Q | 0.559 | A | 0.050 |
| E | 0.482 | R | −0.287 |
| P | 0.253 | E | −0.365 |
| A | 0.182 | N | −0.435 |
| K | 0.036 | D | −1.218 |
| D | −0.554 | G | −1.552 |
| R | −0.581 | P | −1.644 |

TABLE 12

| Position 142 - WT - R | | Position 150 - WT - P | |
|---|---|---|---|
| Mutant | ΔΔG (kcal/mol) | Mutant | ΔΔG (kcal/mol) |
| I | 1.410 | W | 1.901 |
| L | 0.633 | V | −1.721 |
| F | 0.536 | I | −1.880 |
| W | 0.526 | F | −2.109 |
| V | 0.464 | E | −2.148 |
| Y | 0.278 | T | −2.223 |
| M | −0.005 | L | −2.258 |
| Q | −0.171 | C | −2.404 |
| S | −0.290 | K | −2.634 |
| T | −0.412 | R | −2.667 |
| C | −0.413 | Y | −3.002 |
| D | −0.446 | M | −3.215 |
| A | −0.604 | H | −3.221 |
| H | −0.671 | A | −3.228 |
| K | −0.722 | S | −3.244 |
| N | −0.929 | N | −3.595 |
| E | −1.159 | D | −4.183 |
| G | −1.479 | Q | −4.387 |
| P | −1.537 | G | −4.422 |

TABLE 13

| Position 159 - WT - I | | Position 184 - WT - G | |
|---|---|---|---|
| Mutant | ΔΔG (kcal/mol) | Mutant | ΔΔG (kcal/mol) |
| W | −0.029 | W | 2.000 |
| K | −0.067 | L | 1.820 |
| N | −0.204 | F | 1.363 |
| L | −0.239 | E | 0.939 |
| G | −0.324 | I | 0.781 |
| V | −0.370 | Y | 0.684 |
| R | −0.377 | H | 0.588 |
| H | −0.456 | R | 0.532 |
| D | −0.487 | Q | 0.466 |
| C | −0.509 | K | 0.370 |
| E | −0.511 | M | 0.335 |
| F | −0.528 | V | 0.213 |
| S | −0.577 | S | 0.166 |
| M | −0.639 | N | 0.057 |
| A | −0.654 | T | −0.076 |
| Q | −0.705 | A | −0.214 |
| P | −0.747 | C | −0.261 |
| T | −0.769 | D | −0.481 |
| Y | −0.861 | P | −1.065 |

TABLE 14

| Position 238 - WT - A | | Position 321 - WT - Q | |
|---|---|---|---|
| Mutant | ΔΔG (kcal/mol) | Mutant | ΔΔG (kcal/mol) |
| W | 1.680 | T | 2.231 |
| F | 1.418 | V | 2.194 |
| Y | 1.277 | I | 2.143 |
| L | 0.709 | L | 2.138 |
| C | 0.439 | F | 1.739 |
| M | 0.102 | M | 1.538 |
| V | 0.049 | C | 0.700 |
| I | 0.035 | A | 0.549 |
| T | −1.061 | S | 0.413 |
| H | −1.463 | W | 0.348 |
| S | −1.511 | K | −0.073 |
| G | −2.541 | E | −0.298 |
| Q | −2.969 | N | −0.636 |
| N | −3.420 | H | −0.765 |
| D | −4.076 | R | −1.033 |
| P | −4.954 | Y | −1.102 |
| K | −4.984 | D | −1.442 |
| R | −4.987 | G | −2.013 |
| E | −4.989 | P | −2.260 |

All sets of mutations (or combinations thereof) will result in an enzyme that is highly soluble, can function (and is stable) at temperatures at or greater than the wild-type enzyme, and has a longer lifetime is a bio-industrial process. All potential mutations are shown in Table 15, below. Cavity filling potential accounts for 3.3% of all enzyme sequence space, whereas solubility and other sites opportunities account for 1.2% and 2.7% respectively. Hence, only 7.2% of all enzyme amino acids across the entire sequence were calculated to be useful to improve thermostability and/or solubility based on the calculations performed here.

TABLE 15

| | Mutation | DDG (kcal/mol) |
|---|---|---|
| Cavity Filling Mutations | | |
| | G12P | 1.7 |
| | A13Y | 2.7 |
| | A18L | 2.8 |
| | S19Y | 3.0 |
| | S31L | 2.1 |
| | A34L | 2.3 |

TABLE 15-continued

| | Mutation | DDG (kcal/mol) |
|---|---|---|
| | G50L | 1.6 |
| | A103I | 2.3 |
| | G119L | 2.5 |
| | G184W | 2.0 |
| | A238W | 1.7 |
| Surface Charge Mutations | | |
| | A58S | 0.3 |
| | L89S | −0.3 |
| | R142S | −0.3 |
| | I159S | −0.6 |
| Free Energy Mutations | | |
| | N15F | 1.7 |
| | M46W | 1.7 |
| | A49G | 2.2 |
| | E80L | 1.5 |
| | R83L | 3.4 |
| | Q95L | 1.5 |
| | Q141I | 2.1 |
| | P150W | 1.9 |
| | Q321T | 2.2 |

Figure 5:
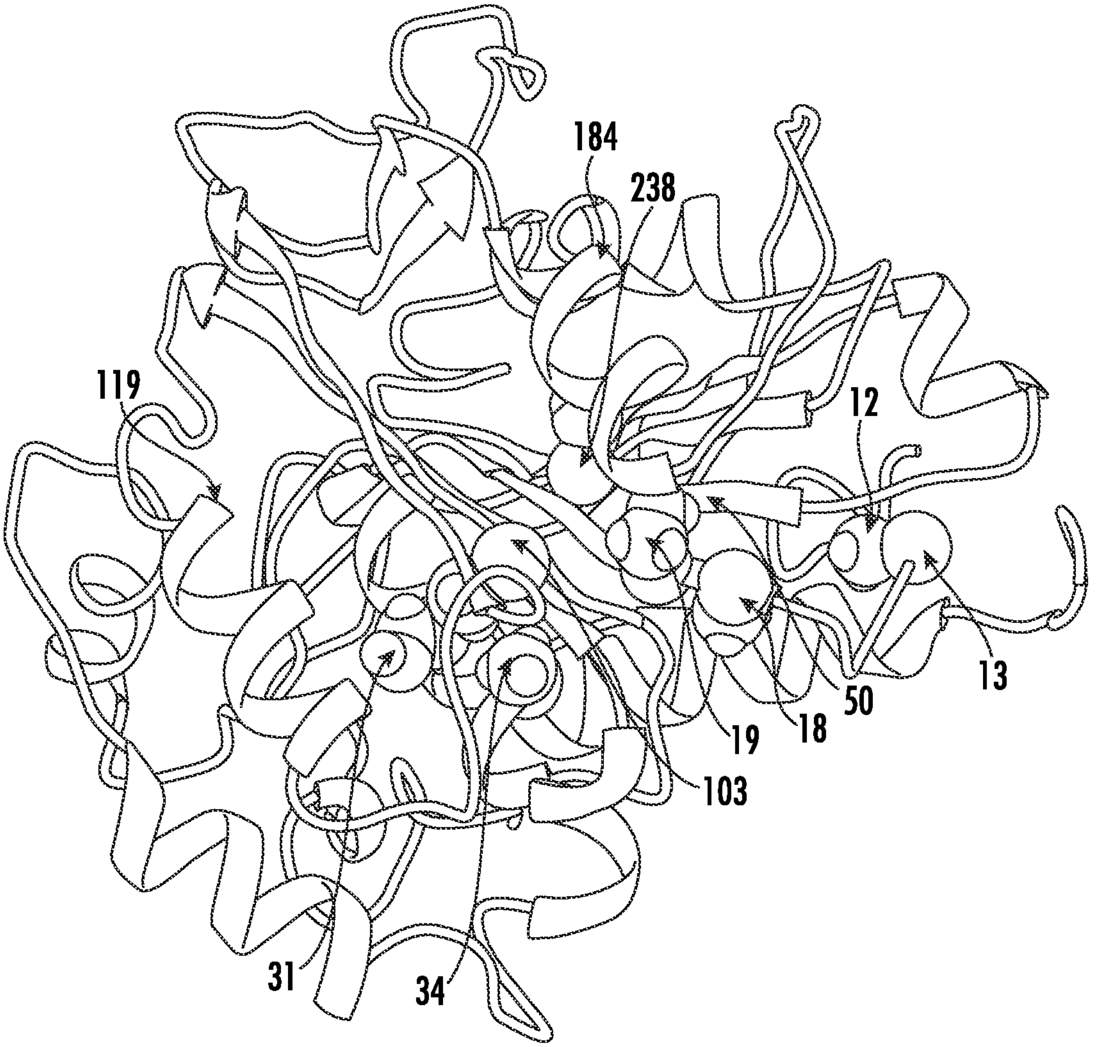
FIG. 5 provides a molecular model of a modified PHBDase showing the position of 11 cavity/void filling stability mutations as compared to an *H. aquamarina* wild-type PHBDase.
Figure 6:
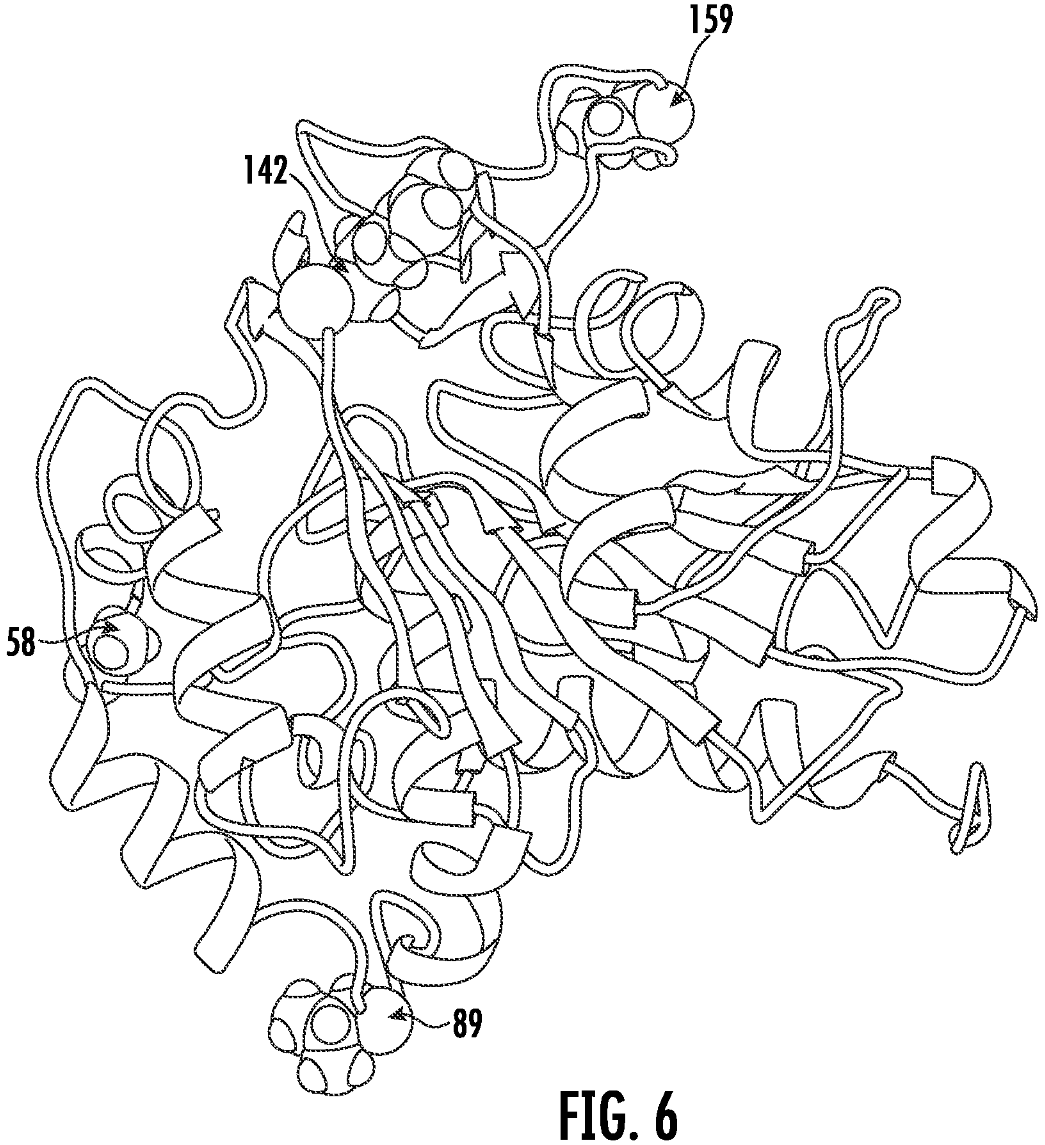
FIG. 6 provides a molecular model of a modified PHBDase showing the position of 4 surface charge stability mutations as compared to an *H. aquamarina* wild-type PHBDase.
Figure 7:
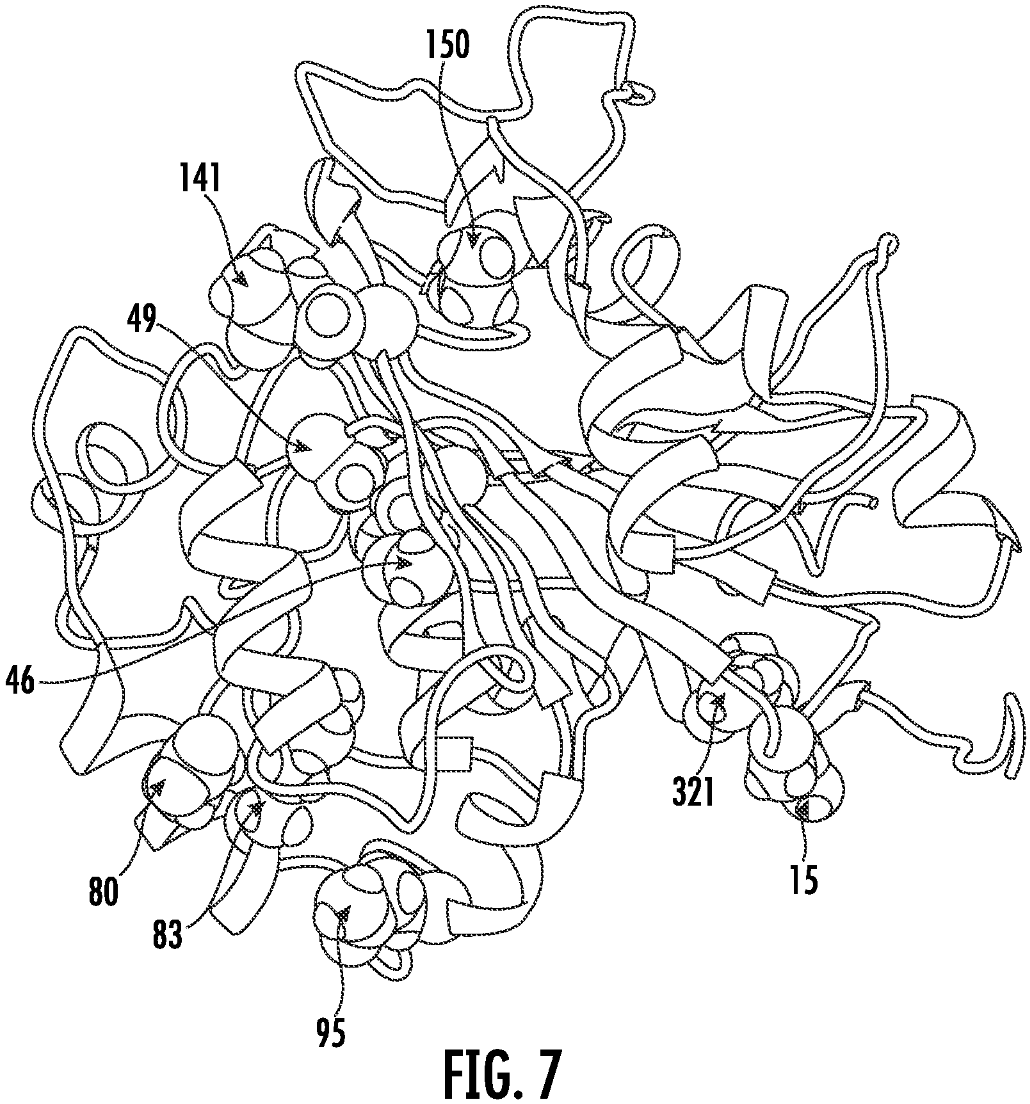
FIG. 7 provides a molecular model of a modified PHBDase showing the position of 9 stability mutations as compared to an *H. aquamarina* wild-type PHBDase.

The 11 cavity-filling mutations of Table 3 are visualized in the protein 3D model of FIG. 5. FIG. 6 provides a 3D visualization of the 4 surface-charge mutations of Table 3, and FIG. 7 illustrates the 9 mutations developed by the Gibbs free energy analysis approach.

Example 4

Three mutants were constructed using the procedures described in Example 2, and the enzymes were purified to homogeneity. The first mutant was designated KCC-H1 (SEQ ID NO: 8) and incorporated all four surface-charge stabilizing mutations of Table 3; the second mutant was designated KCC-H2 (SEQ ID NO: 10) and incorporated these four mutations plus the 11 potential cavity-filling mutations of Table 3; and the third mutant was designated KCC-H3 (SEQ ID NO: 12) and incorporated the four charge-stabilizing mutants plus the nine mutants determined by the Gibbs free energy analysis. The mutants were assessed for stability, enzymatic activity, and pH optima as described above. The KCC-H1 mutant exhibited a significant amount of soluble-expressed enzyme per liter of culture—An average of 2.4-fold more protein, as is shown in Table 16. When the KCC-H1 mutations were combined with either the cavity-filling mutations (KCC-H2) or the free-energy method-derived mutants (KCC-H3), the level of solubility remained at the elevated KCC-H1 level. The overall mutation background had very little effect on molecular weight or isoelectric point as is seen in Table 17. As shown in Table 18, KCC-H1 had a temperature of maximal activity identical to the wild-type enzyme. However, both KCC-H2 and KCC-H3 showed a significant increase in thermal stability, as indicated by their temperature of maximal activity. Numbers are the mean of two independent determinations. Values in parentheses in the Tables are the standard deviation. Values are the mean of three independent determinations. Numbers in parentheses are the standard deviation.

TABLE 16

| Protein | Solubility (mg/L) |
|---|---|
| Wild-type | 9.2 (0.6) |
| KCC-H1 | 22.5 (0.5) |
| KCC-H2 | 23.7 (0.6) |
| KCC-H3 | 21.2 (0.5) |

TABLE 17

| Protein | MW (kDa) | pI |
|---|---|---|
| Wild-type | 35.7 | 4.4 |
| KCC-H1 | 35.6 | 4.3 |
| KCC-H2 | 36.4 | 4.3 |
| KCC-H3 | 35.7 | 4.3 |

TABLE 18

| Protein | $K_m$ (μM) | $k_{cat}$ ($S^{-1}$) | $k_{cat}K_m^{-1}$ ($S^{-1}\mu M^{-1}$) | $pH_{opt}$ | $T_{opt}$ (° C.) |
|---|---|---|---|---|---|
| KCC-H1 | 14.2 (0.2 | 3.9 (0.1) | 0.27 | 6.4 | 40.1 (0.2) |
| KCC-H2 | 13.7 (0.1) | 4.3 (0.1) | 0.31 | 6.4 | 57.5 (0.2) |
| KCC-H3 | 11.4 (0.2) | 4.1 (0.1) | 0.36 | 6.3 | 50.4 (0.1) |

As shown, KCC-H2 can function 17.4° C. higher than the wild-type enzyme (57.5° C. versus 40.1° C.) and KCC-H3 can function 10.3° C. higher than the wild-type enzyme (50.4° C. versus 40.1° C.). This indicates that both sets of mutations do indeed increase the thermal activity of the *Halomonas* enzyme. $T_{opt}$ is utilized versus a thermodynamic analysis because all the enzymes contain disulfide bonds which induce enzyme precipitation at the temperature of optimal activity. Hence, these methods can be used to increase the thermostability of a halophilic enzyme to significant degree. In fact, it may be possible to dial-in desired thermal activity levels by using different subsets of these mutations—meaning using fewer mutations or choosing between the cavity-filling- and direct free-energy-derived mutants. The result of KCC-H1, H2, and H3 mutants is that the enzyme is significantly more soluble, which makes it more economical to use in an industrial process. Two of the mutants are also more thermophilic (KCC-H2 and KCC-H3), which can additionally be used to kill mesophilic bacteria contaminating the input sample.

Figure 8:
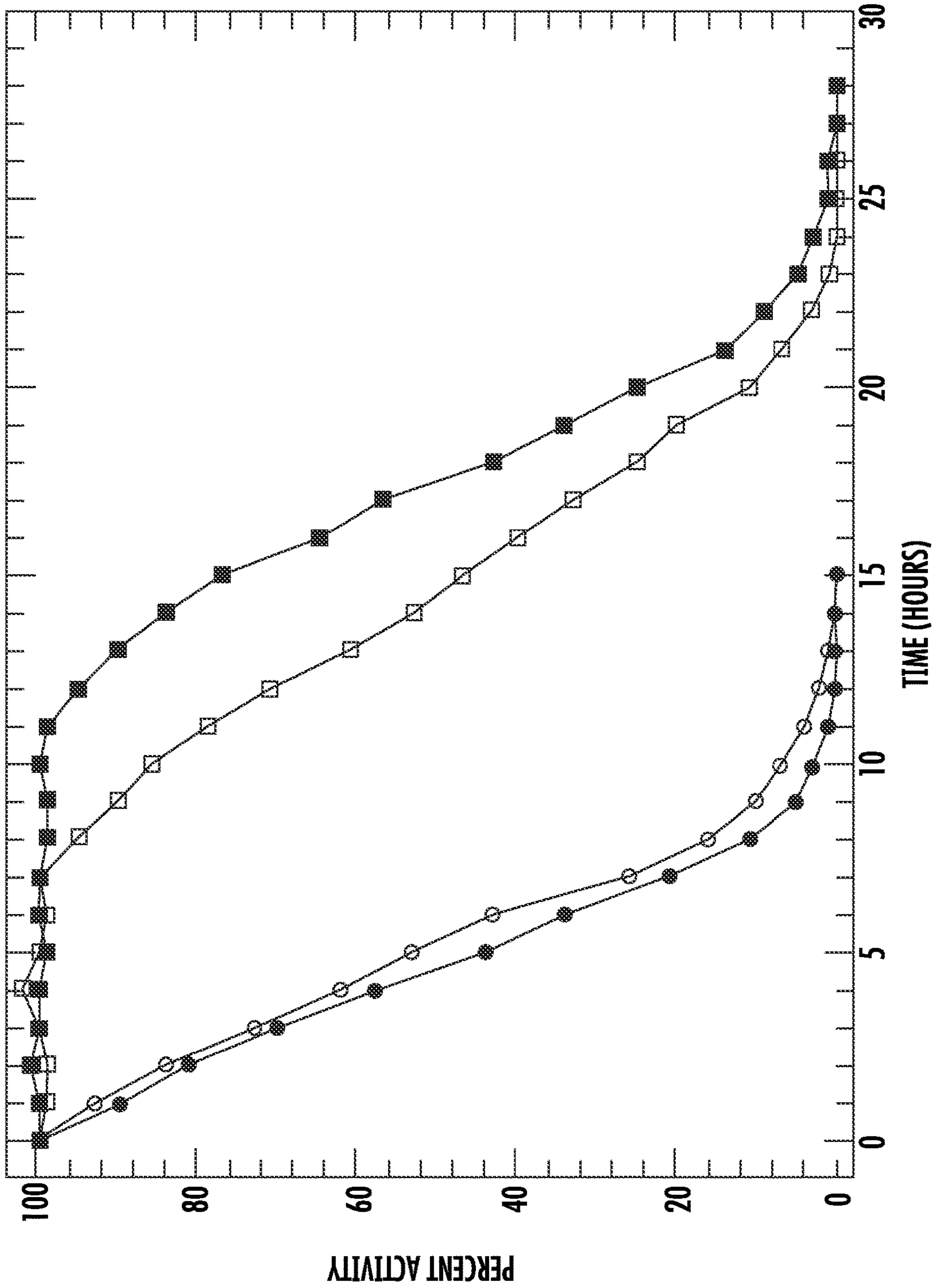
FIG. 8 graphically compares the percent maximum PHBDase enzymatic activity as a function of time at 37° C. for a modified enzyme as described herein and a wild-type halophilic PHBDase.

All three enzyme mutants were longer-lived at a reduced temperature compared to the wild-type PHBDase as is shown in FIG. 8. In FIG. 8, Activity at t=0 was arbitrarily set to 100% activity. Open circles—Wild-type; Closed circles—KCC-H1; Open squares—KCC-H3; Closed squares—KCC-H2. The wild-type enzyme had a half-life of 4.5 hours at 37° C. At this same temperature, KCC-H1 had a half-life of 5.5 hours (most likely driven by increased fundamental solubility). The KCC-H2 and the KCC-H3 mutants had half-lives of 17.5 and 14.0 hours, respectively. Thus, the stability mutants manifested themselves in an increased Topy and half-life, both parameters of which are valued in an industrial process.

While certain embodiments of the disclosed subject matter have been described using specific terms, such description is for illustrative purposes only, and it is to be understood that changes and variations may be made without departing from the spirit or scope of the subject matter.

What is claimed is:

1. A method for treatment of a post-consumer product, the method comprises:

within a bioreactor, contacting a post-consumer product with a polypeptide in the presence of a salt, wherein the salt is present at a concentration of about 1 M or greater, the post-consumer product comprises a polyhydroxyalkanoate, the polypeptide catalyzes degradation of the polyhydroxyalkanoate, and the contact takes place at a temperature of about 40° C. or greater;

wherein the polypeptide comprises a modified polyhydroxyalkanoate depolymerase that includes one or more single-site mutations as compared to SEQ ID NO: 5, wherein the modified polyhydroxyalkanoate depolymerase has a solubility of about 10 mg/L or greater and at least one of the one or more single-site mutations has a positive ΔΔG value.

2. The method of claim 1, wherein the polypeptide comprises a modified polyhydroxyalkanoate depolymerase that includes four or more single-site mutations as compared to SEQ ID NO: 5.

3. The method of claim 1, wherein the salt is present at a concentration of about 1.5 M or greater, and/or the contact takes place at a temperature of about 45° C. or greater.

4. The method of claim 1, wherein the post-consumer product comprises a post-consumer personal care product.

5. The method of claim 4, wherein prior to the contact, the post-consumer personal care product is contaminated with a bodily waste that comprises blood, urine, feces, or menstrual fluid.

* * * * *